US007696335B2

(12) United States Patent
Holt et al.

(10) Patent No.: US 7,696,335 B2
(45) Date of Patent: *Apr. 13, 2010

(54) KITS FOR MULTIPLE NON-CROSS REACTING RECOMBINATION REACTIONS UTILIZING LOXP SEQUENCES

(75) Inventors: Robert A. Holt, North Vancouver (CA); Perseus I. Missirlis, Vancouver (CA)

(73) Assignee: BC Cancer Agency, Vancouver, BC (CA)

( * ) Notice: Subject to any disclaimer, the term of this patent is extended or adjusted under 35 U.S.C. 154(b) by 643 days.

This patent is subject to a terminal disclaimer.

(21) Appl. No.: 11/546,735

(22) Filed: Oct. 12, 2006

(65) Prior Publication Data

US 2007/0087366 A1    Apr. 19, 2007

Related U.S. Application Data

(60) Provisional application No. 60/725,630, filed on Oct. 13, 2005.

(51) Int. Cl.
*C07H 21/02* (2006.01)
*C07H 21/04* (2006.01)
*C12Q 1/68* (2006.01)

(52) U.S. Cl. .......................... 536/23.1; 536/24.2; 435/6

(58) Field of Classification Search ....................... None
See application file for complete search history.

(56) References Cited

U.S. PATENT DOCUMENTS

| | | | | |
|---|---|---|---|---|
| 4,673,640 | A | 6/1987 | Backman | 435/68 |
| 4,959,317 | A | 9/1990 | Sauer | 435/462 |
| 5,227,288 | A | 7/1993 | Blattner | 435/6 |
| 5,434,066 | A | 7/1995 | Bebee | 435/172.3 |
| 5,830,707 | A | 11/1998 | Bushman | 435/69.7 |
| 5,888,732 | A | 3/1999 | Hartley | 435/6 |
| 5,919,676 | A | 7/1999 | Graham | 435/172.3 |
| 5,965,444 | A | 10/1999 | Ashikari | 435/483 |
| 6,270,969 | B1 | 8/2001 | Hartley | 435/6 |
| 6,277,608 | B1 | 8/2001 | Hartley | 435/91.4 |
| 6,410,317 | B1 | 6/2002 | Farmer | 435/320.1 |
| 6,458,592 | B1 | 10/2002 | Jakobovits | 435/455 |
| 6,465,254 | B1 | 10/2002 | Saito | 435/462 |
| 6,509,156 | B1 | 1/2003 | Stewart | 435/6 |
| 6,720,140 | B1 | 4/2004 | Hartley | 435/6 |
| 6,720,475 | B1 | 4/2004 | Baszczynski | 800/278 |
| 6,890,726 | B1 | 5/2005 | Sauer | 435/7.4 |
| 6,992,235 | B2 | 1/2006 | Bode | 800/21 |
| 2003/0153055 | A1 | 8/2003 | Miles | 435/91.2 |
| 2003/0157662 | A1 | 8/2003 | Gerard | 435/91.2 |
| 2004/0229229 | A1 | 11/2004 | Cheo | 435/6 |
| 2004/0265863 | A1 | 12/2004 | Chesnut | 435/6 |
| 2005/0208530 | A1 | 9/2005 | Chesnut | 435/6 |

OTHER PUBLICATIONS

Missirlis, et al. (2006) BMC Genomics, 7(73): 1-13.*

Abremski et al, "Bacteriophage P1 Cre-loxP site-specific recombination," J. Biol. Chem., 261: 391-396 (1986).

Abremski et al, "Properties of a mutant Cre protein that alters the topological linkage of recombination products," J. Mol. Biol., 202: 59-66 (1988).

Arakawa et al, "Mutant loxP vectors for selectable marker recycle and conditional knock-outs," BMC Biotechnology, 1: 7 (2001).

Araki et al, "Targeted integration of DNA using mutant lox sites in embryonic stem cells," Nucleic Acids Research, 25: 868-872 (1997).

Araki et al, "Site-directed integration of the Cre gene mediated by Cre recombinase using a combination of mutant lox sites," Nucleic Acids Research, 30: e103 (2002).

Baer et al, "Coping with kinetic and thermodynamic barriers: RMCE, an efficient strategy for the targeted integration of transgenes," Curr. Opin. Biotechnol., 12: 473-480 (2001).

Branda et al, "Talking about a revolution: the impact of site-specific recombinases on genetic analysis in mice," Developmental Cell, 6: 7-28 (2004).

Brasch et al, "ORFeome cloning and systems biology: standardized mass production of the parts from the parts-list," Genome Research, 14: 2001-2009 (2004).

Chatterjee et al, "Mutually exclusive recombination of wild-type and mutant loxP sites in vivo facilitates transposon-mediated deletions from both ends of genomic DNA in PACs," Nucleic Acids Research, 32: 5668-5676 (2004).

Cheo et al, "Concerted assembly and cloning of multiple DNA segments using in vitro site-specific recombination: Functional analysis of multi-segment expression clones," Genome Research, 14: 2111-2120 (2004).

Hoess et al, "The role of the loxP spacer region in P1 site-specific recombination," Nucleic Acids Research, 14: 2287-2300 (1986).

Hoess et al, "Isolation and characterization of intermediates in site-specific recombination," Proc. Natl. Acad. Sci., 84: 6840-6844 (1987).

Hope et al, "Feasibility of genome-scale construction of promoter:: reporter gene fusions for expression in *Caenorhabditis elegans* using a multisite Gateway recombination system," Genome Research, 14: 2070-2075 (2004).

Kondo et al, "Simultaneous on/off regulation of transgenes located on a mammalian chromosome with Cre-expressing adenovirus and a mutant loxP," Nucleic Acids Research, 31: e76 (2003).

Langer et al, "A genetic screen identifies novel non-compatible loxP sites," Nucleic Acids Research, 30: 3067-3077 (2002).

(Continued)

*Primary Examiner*—Robert M Kelly
(74) *Attorney, Agent, or Firm*—Stephen C. Macevicz

(57) ABSTRACT

The invention provides methods, kits, and compositions comprising novel mutant loxP sites. Such sites are particularly useful for procedures requiring multiple site-specific recombination reactions, including deletions or insertions of multiple genes or other sequences in the same organism, staged insertions or deletions of genes of the same organism at different times, assembly of large polynucleotide constructs by serial site-specific recombination, and the like. In one aspect, compositions of the invention includes particular mutant spacer oligonucleotides of loxP recombination elements, the recombination elements themselves, and pairs of non-promiscuous mutant loxP sites.

14 Claims, 8 Drawing Sheets

OTHER PUBLICATIONS

Sauer, "Multiplex Cre/lox recombination permits selective site-specific DNA targeting to both a natural and an engineered site in the yeast genome," Nucleic Acids Research, 24: 4608-4613 (1996).

Zhang et al, "Cre recombinase-mediated inversion using lox66 and lox71: method to introduce conditional point mutations into the CREB-binding protein," Nucleic Acids Research, 30: e90 (2002).

* cited by examiner

Mutant LoxP Screening Procedure

1. Design two separate pools of loxP oligonucleotides with degenerate spacers:

2. Design tailed primers for PCR amplification of oligonucleotides:

3. PCR amplification

4. Digest, subclone into pUC19

KITS FOR MULTIPLE NON-CROSS REACTING RECOMBINATION REACTIONS UTILIZING LOXP SEQUENCES

This application claims priority from U.S. provisional application Ser. No. 60/725,630 filed 13 Oct. 2005, which is hereby incorporated by reference in its entirety.

FIELD OF THE INVENTION

The invention relates generally to methods and compositions for constructing recombinant DNA molecules, and more particularly, to methods and compositions for serial site-specific recombination using mutant loxP sequences.

BACKGROUND

Cre-loxP recombination is an important tool in molecular genetics. Cre ("Causes recombination") recombinase from bacteriophage P1 recognizes a specific 34 basepair (bp) target sequence, termed loxP, composed of an 8 bp spacer region flanked by two identical 13 bp inverted repeats (Table 1), e.g. Hoess et al Proc. Natl. Acad. Sci., 79: 3390-3402 (1982). Each base in the spacer region is conventionally named 1, 2, 3, 4, 5, 6, 7, or 8, according to its order (5'→3') in the sequence. Cre-loxP sites mediate site specific intra- or interstrand exchange of DNA molecules catalyzed by Cre recombinase. Depending on the location and the orientation of these sites, they can invert, insert, delete or exchange fragments of DNA in prokaryotic or eukaryotic systems, e.g. Sauer, Mol. Cell. Biol., 7: 2087-2096 (1987); Sauer et al, Proc. Natl. Acad. Sci., 85: 5166-5170 (1988); Sauer et al, Nucleic Acids Research, 17: 147-161 (1989). Orientation of insert DNA post-recombination is dependent on the orientation of the sites prior to the reaction, with sites in the same orientation on a given DNA strand mediating excision of intervening sequence and sites in opposite orientation mediating inversion of intervening sequence. Since the excision reaction is kinetically favored over the insertion reaction, gene deletion/inactivation experiments are straightforward to engineer by flanking the target sequence with loxP sites. The difficulty in implementing a stable DNA insertion is that the insertion reaction results in the presence of two loxP sites in cis configuration in the post-recombination product, which themselves become substrates for Cre and lead to rapid excision of the inserted component polynucleotide.

Two classes of variant loxP sites are available to engineer stable Cre-loxP integrative recombination. Both exploit sequence mutations in the Cre recognition sequence, either within the 8 bp spacer region or the 13-bp inverted repeats. Spacer mutants such as lox511, lox5171, lox2272, m2, m3, m7, and m11 recombine readily with themselves but have a markedly reduced rate of recombination with the wild-type site, e.g. Hoess et al, Nucleic Acids Research, 14: 2287-2300 (1986); Lee et al, Gene, 216: 55-65 (1998); Langer et al, Nucleic Acids Research, 30: 3067-3077 (2002). This class of mutants has been exploited for DNA insertion by Recombinase Mediated Cassette Exchange (RMCE), e.g. Seibler et al, Biochemistry, 36: 1740-1747 (1997); Schlake et al, Biochemistry, 33: 12746-12751 (1994); Baer et al, Curr. Opin. Biotech., 12: 473-480 (2001). Inverted repeat mutants represent the second class available and contain altered bases in the left inverted repeat (LE mutant) or the right inverted repeat (RE mutant). The LE mutant, lox71, has 5 bp on the 5' end of the left inverted repeat that are changed from the wild type sequence to TACCG, e.g. Albert et al, Plant J., 7: 649-659 (1995); Araki et al, Nucleic Acids Research, 25: 868-872 (1997). Similarly, the RE mutant, lox66, has the five 3'-most bases changed to CGGTA. Inverted repeat mutants are used for integrating plasmid inserts into chromosomal DNA with the LE mutant designated as the "target" chromosomal loxP site into which the "donor" RE mutant recombines. Post-recombination, loxP sites are located in cis, flanking the inserted component polynucleotide. The mechanism of recombination is such that post-recombination one loxP site is a double mutant (containing both the LE and RE inverted repeat mutations) and the other is wild type, e.g. Van Duyne et al, Annu. Rev. Biophys. Biomol. Struct., 30: 87-104 (2001); Lee et al, Prog. Nucleic Acid Res. Mol. Biol., 80: 1-42 (2005); Lee et al, J. Mol. Biol., 326: 397-412 (2003). The double mutant is sufficiently different from the wild-type site that it is unrecognized by Cre recombinase and the inserted component polynucleotide is not excised. Recently, spacer and inverted repeat mutants have been combined to increase the specificity and stability of integrative recombination, e.g. Langer et al (cited above); Araki et al, Nucleic Acids Research, 30: e103 (2002).

Previously, novel spacer mutants have been discovered by mutating bases or by generating a set of potential spacer mutants and testing recombination between these spacers with the wild-type loxP site, e.g. Langer et al (cited above); Lee et al (Gene, cited above). In particular, Lee et al used an in vitro assay that evaluated the recombination efficiency of 24 spacers with 1 bp substitutions and 30 spacers with 2 bp substitutions from the sequence of the wild-type loxP. Their data suggested that homology was required at positions 2-5 and positions 6-7 for efficient strand exchange and resolution of a Holiday junction, whereas positions 1 and 8 had relaxed homology requirements. They concluded that homology was essential to achieve recombination rates between mutant loxP spacers comparable to that of the wild-type sequence. Their success with the lox2272 mutant suggested that positions 2 and 7 were particularly important in blocking promiscuous recombination.

The above work is important because recombination systems, such Cre-loxP and others, provide a means for making and/or manipulating large polynucleotide constructs that are useful in fields, such as synthetic biology, metabolic engineering, and the like, where practitioners seek to improve cellular activities by large-scale manipulation of enzymatic, transport, and regulatory functions of cells, e.g. Bailey, Science, 252: 1668-1674 (1991). It would be highly useful to such fields if there were available additional recombination elements that could be used together without cross-reactivity for the purpose of constructing large polynucleotide constructs, particularly through successive cycles of site-specific recombination.

SUMMARY OF THE INVENTION

The invention provides methods, kits, and compositions comprising novel mutant loxP sites. Such sites are particularly useful for procedures requiring multiple site-specific recombination reactions, including deletions or insertions of multiple genes, or other sequences, in the same organism, staged insertions or deletions of genes of the saint organism at different times, assembly of large polynucleotide constructs by serial site-specific recombination, and the like. In one aspect, compositions of the invention include spacer oligonucleotides of Table II as components of loxP recombination elements, as well as the recombination elements themselves. In another aspect, compositions of the invention include mutant loxP spacer regions that give rise to non-promiscuous loxP recombination elements. In one embodiment, such mutant loxP spacer regions are selected from the following group:

GTATAGTA, GGCTATAG, TCGTAGGC, GTGTATTT, GTGTACGG,

GCGTATGT, TTGTATGG, GGATAGTA, AGGTATGC, GGTTACGG,

TTTTACGT, GAGTACGC, and GTGTACGC.

In another aspect, compositions of the invention includes pairs of mutant loxP recombination elements that recombine with one another. In one embodiment, such pairs are defined as follows: a first member of a pair is defined as:

$LE_1$-$S_1$-$RE_1$ and a second member of the pair is defined as:

$LE_2$-$S_2$-$RE_2$ where:

$LE_1$ is a mutant or wild type left end loxP site Cre recognition sequence and $RE_1$ is a mutant or wild type right end loxP site Cre recognition sequence such that whenever $LE_1$ is a wild type sequence, $RE_1$ is a mutant sequence, and whenever $LE_1$ is a mutant sequence, $RE_1$ is a wild type sequence;

$LE_2$ is a mutant or wild type left end loxP site Cre recognition sequence and $RE_2$ is a mutant or wild type right end loxP site Cre recognition sequence such that whenever $LE_2$ is a wild type sequence, $RE_2$ is a mutant sequence, and whenever $LE_2$ is a mutant sequence, $RE_2$ is a wild type sequence; with the proviso that whenever $LE_1$ is a mutant sequence, then $LE_2$ is a wild type sequence; and $S_1$ and $S_2$ are members of a pair of mutant loxP spacer regions selected from Table III. Left and right Cre recognition sequences, that is right or left inverted repeat sequences, may be selected from known sequences or they may be synthesized and tested using assays such as those described below.

In another aspect, $S_1$ and $S_2$ are loxP spacer regions each having the same sequence selected from the group consisting of:

TTTTAGGT, GGCTATAG, TCGTAGGC, GGTTACGG, GGATAGTA,

GCGTATGT, GTATAGTA, GCATAGGC, GTGTATTT, GTGTAGTC,

GTGTAGGA, TTGTATGG, GGGTAGCG, GGGTATTC, GAGTACGC,

GGTTAGGC, TGCTATGT, GGGTAGAC, TGGTACTT, TGGTATGC,

CGGTAGGG, GGGTAGAT, GGGTAGGT, GGGTAAGC, GGGTAGTT,

GTGTAGGC, TGGTAGGG, GTGTAGGG, GGGTAGGT, GGGTAGGG, and GGGTAGGC, or $S_1$ and $S_2$ are loxP spacer regions such that whenever $S_1$ is selected from column 1 below $S_2$ is the sequence in the column 2 of the same row as $S_1$, and whenever $S_1$ is selected from column 2 $S_2$ is the sequence in column 1 of the same row as $S_1$:

| Column 1 | Column 2 |
|---|---|
| TGGTAGGC | TGGTAGGT |
| GGGTATGC | GGGTATGG |
| GTGTAGTT | GTGTAGTG |

-continued

| Column 1 | Column 2 |
|---|---|
| GGGTATGG | GTGTATGG |
| TGGTAGTC | TGGTAGTG |
| GTGTACGG | GTGTACGC |
| TGGTAGGA | GGGTAGGA |
| GGGTATAC | GTGTATAC |
| GGGTAAGT | GGGTATGT |
| TGGTAGTC | GGGTAGTC |
| GTGTAAGA | GTGTAAGG |
| GGGTATGA | GGGTAGGA |
| GGGTATAC | GGCTAGGC |
| GAGTAGGA | GAGTAGGG |
| TTGTATGC | GTGTATGT |
| TTGTAGGC | CTGTAGGG |

In another aspect, compositions of the invention comprise pairs of oligonucleotides comprising mutant loxP sequences of the invention that react with each other, but which are substantially unreactive with other loxP sequences, i.e. are non-promiscuous. In one embodiment of this aspect, $S_1$ and $S_2$ are loxP spacer regions either each having the same sequence selected from the group consisting of:

GTATAGTA, GGCTATAG, TCGTAGGC, GTGTATTT, GCGTATGT,

TTGTATGG, GGATAGTA, AGGTATGC, GGTTACGG, TTTTAGGT, and GAGTACGC, or, $S_1$ is GTGTACGC whenever $S_2$ is GTGTACGG; and $S_2$ is GTGTACGC whenever $S_1$ is GTGTACGG. Such non-promiscuous spacer sequences are particularly useful in operations where more than one recombination reaction is desired, such as multiple gene deletions or insertion in the same construct or genome, or serial site-specific recombination. As used herein, "non-promiscuous" in reference to a loxP spacer sequence means that loxP sites containing such sequence (or pair of non-self recombining sequences) are substantially unreactive, or non-cross-reactive, with loxP sites containing other spacer sequences. In one aspect, non-promiscuous means that such sequence or pairs of sequences cross-react with less than 100 other loxP sites having a spacer selected from the set defined by formula NNNTANNN; in another aspect, such cross-reactivity is with less than 50 of such sites; in another aspect, such cross-reactivity is with less than of 20 such sites; and in another aspect, such cross-reactivity is with less than of 10 such sites.

In still another aspect, the invention provides a method for screening for mutant recombination elements, such as mutant loxP recombination elements, that have favorable properties, such as increased cross-reactivity as among wild type elements or other mutant elements, decreased cross-reactivity as among wild type elements or other mutant elements, exclusive reactivity as between pairs or limited subsets of recombination elements, and the like.

In particular, the invention provides compositions, methods, and kits for carrying out site-specific recombination reactions. In one aspect, the availability of multiple pairs of non-cross reacting site-specific recombination elements makes possible to conduct several successive site-specific recombination reactions with the same nucleic acid construct or genome, such as making several gene insertions, conversions, or deletions in the same organism, assembling multiple component polynucleotides into a single nucleic acid construct, and the like. The invention has applications in a wide variety of fields, including biological and medical research, synthetic biology, and metabolic engineering.

DETAILED DESCRIPTION OF THE INVENTION

The practice of the present invention may employ, unless otherwise indicated, conventional techniques and descriptions of organic chemistry, molecular biology (including recombinant techniques), cell biology, biochemistry, and immunology, which are within the skill of the art. Such conventional techniques include, but are not limited to, vector construction, microbial host transformation, selection and application of genetic markers, manipulation of large polynucleotide fragments, preparation of synthetic polynucleotides, application of recombination systems, nucleic acid sequencing and analysis, and the like. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies. A Laboratory Manual, Cells: A Laboratory Manual, PCR Primer: A Laboratory Manual, and Molecular Cloning: A Laboratory Manual* (all from Cold Spring Harbor Laboratory Press), Stryer, L. (1995) *Biochemistry* (4th Ed.) Freeman, New York, Gait, *"Oligonucleotide Synthesis: A Practical Approach"* 1984, IRL Press, London, Nelson and Cox (2000), *Lehninger, Principles of Biochemistry* 3$^{rd}$ Ed., W.H. Freeman Pub., New York, N.Y. and Berg et al. (2002) *Biochemistry,* 5$^{th}$ Ed., W.H. Freeman Pub., New York, N.Y., Casali et al, editors, *E. Coli* Plasmid Vectors: Methods and Applications (Humana Press, Totowa, N.J., 2003), all of which are herein incorporated in their entirety by reference for all purposes.

Recombination Reactions with Mutant LoxP Sequences

Figure 2:
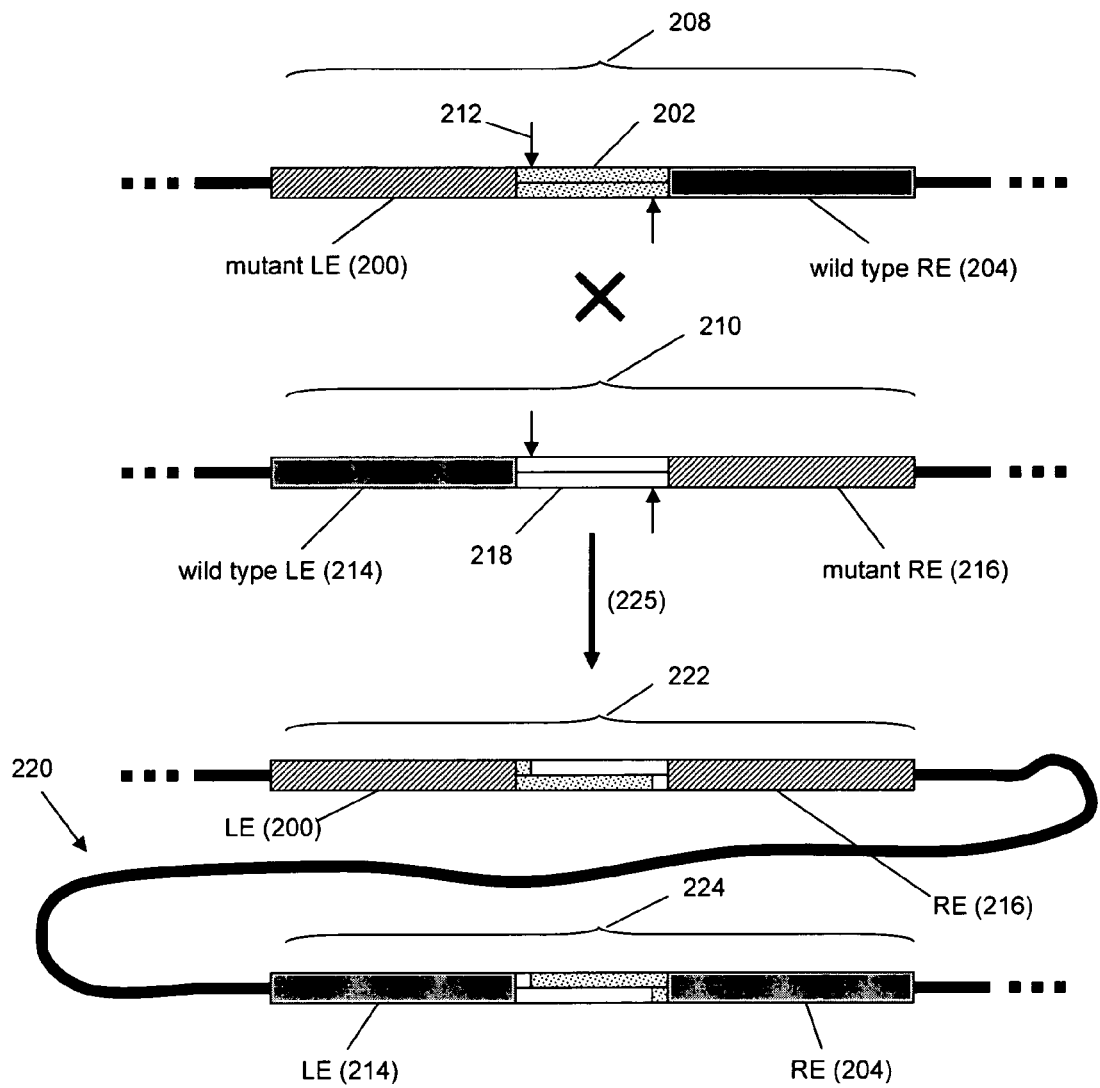
FIG. 2 illustrates a recombination reaction between two single mutation loxP sites that results in a mutation-free site and a double mutation site in the recombinant product.

In one aspect, the invention provides pairs of loxP sites may be used for assembling nucleic acid constructs, such as replacement genomes or large circular DNA molecules. As illustrated in FIG. 2, loxP sites comprise a left end (200), i.e. "LE" Cre recognition site, or "arm," a right end (204), i.e. "RE," Cre recognition site, or "arm," and sandwich between the LE and RE arms, a spacer region (402). In most wild type and mutant loxP sites, the LE and RE arms (200 and 204) are each 13 basepair in length, and the spacer region (202) is 8 basepairs in length. Also, in the wild type and in most mutant loxP sites, the LE and RE arms are inverted repeats. The loxP wild type sequence, as well as the sequences of several mutant loxP sites are shown in Table I.

TABLE I (deviations from wild type shown in lower case)

| Site Name | LE | spacer | RE | SEQ ID NO |
|---|---|---|---|---|
| loxP wild type | ATAACTTCGTATA | ATGTATGC | TATACGAAGTTAT | 1 |
| lox511 | ATAACTTCGTATA | ATGTATaC | TATACGAAGTTAT | 2 |
| lox5171 | ATAACTTCGTATA | ATGTgTaC | TATACGAAGTTAT | 3 |
| lox2272 | ATAACTTCGTATA | AaGTATcC | TATACGAAGTTAT | 4 |
| m2 | ATAACTTCGTATA | AgaaAcca | TATACGAAGTTAT | 5 |
| m3 | ATAACTTCGTATA | taaTAcca | TATACGAAGTTAT | 6 |
| m7 | ATAACTTCGTATA | AgaTAgaa | TATACGAAGTTAT | 7 |
| m11 | ATAACTTCGTATA | cgaTAcca | TATACGAAGTTAT | 8 |
| lox71 | taccgTTCGTATA | ATGTATGC | TATACGAAGTTAT | 9 |
| lox66 | ATAACTTCGTATA | ATGTATGC | TATACGAAcggta | 10 |

The components of the loxP site may be modified to produce sets of mutant loxP pairs, as illustrated in FIG. 2, which have the following properties: (i) members of a pair react with each other (i.e. to form recombinants), but essentially do not react with other member pairs of the set, and (ii) the product of a reaction between members of a pair are one inoperable loxP site (i.e., Cre is substantially unable to catalyze a recombination involving the site) one active loxP site (i.e., Cre is able to catalyze a recombination involving the site). In one aspect, the latter active loxP site is the wild type loxP site. Such pairs of loxP sites operate as illustrated in FIG. 2. There single mutant loxP site (208) recombines with single mutant loxP site (210) to produce recombinant (220) that has double mutant loxP site (222) and mutant-free loxP site (224). Single mutant loxP site (208) comprises mutant LE (200), wild type RE (202), and spacer region (202). Single mutant loxP site (210) comprises wild type LE (214), mutant RE (216), and spacer region (218). Spacer regions (202) and (218) usually (but not necessarily) have the same sequence within a pair of interacting (or compatible) sites. In one aspect, non-interacting loxP sites have spacer regions with different sequences. A Cre catalyzed recombination of mutant loxP sites (208) and (210) produces (225) a product (220) containing two separate loxP sites in which both mutant arms are brought together and both wild type arms are brought together. In one aspect, mutant loxP sites are selected so that whenever a double mutant loxP is produced it is substantially inoperable with respect to further Cre catalyzed recombination. This prevents undesired recombinations involving the sites when Cre is used in later steps of serial site-specific recombination. In another aspect, the second loxP site of recombinant (220) (which is usually the wild type loxP site) is fully active with other compatible loxP sites (e.g. that have the same spacer region). Thus, such sites may be used to add further component polynucleotides to a replacement genome or pairs of such sites may be used to exchange fragments of a replacement genome, e.g. in a recombinase mediated cassette exchange (RMCE) type of reaction, Seibler and Bode, Biochemistry, 36: 1740-1747 (1997); and Bode et al, U.S. Pat. No. 6,992,235; which references are incorporated by reference. The following references, which are incorporated by reference, provide guidance to those of skill in the art in selecting and using wild type and mutant loxP recombination elements: Hoess et al, Proc. Natl. Acad. Sci., 79: 3398-3402 (1982); Hoess et al, Nucleic Acids Research, 14: 2287-2300 (1986); Hoess et al, Gene, 40: 325-329 (1985); Missirlis et al, BMC Genomics, 7: 73 (2006); Lee et al, Gene, 216: 55-65 (1998); Lee et al, J. Mol. Biol., 326: 397-412 (2003); Saito et al, U.S. Pat. No. 6,465,254; and the like.

Serial Site-Specific Recombination Using Mutant LoxP Sequences

Mutant loxP sequences of the invention may be used alone or with elements from other recombination systems for assembling different component polynucleotides into a single nucleic acid construct. Such assembly is accomplished by combining the component polynucleotides (which are typically a vector or part of a vector) stepwise, or serially, wherein at the conclusion of each step a successively larger nucleic acid construct is obtained. In order to serially assemble different component polynucleotides into a growing nucleic acid construct, a recombinase is selected that is capable of catalyzing separate recombination events with recombination elements having different sequences without the occurrence of significant cross reaction among different recombination elements. Thus, for a successful assembly of a target construct, a sufficient number of different non-cross reacting recombination elements must be available for assembly to be completed. Alternatively, non-cross reacting recombination elements may be re-used in alternating steps of assembly; thus, only two non-cross reacting recombination elements are required, although more than two may be employed in such a re-use strategy. Many recombination systems may be used alone or in combination with one another. Suitable recombination systems include, but are not limited to: 1) linear homologous recombination using two crossover sites near the ends of the sequence of interest, exemplified by a Red/ET system; 2) circle homologous integration followed by a second resolving recombination, exemplified by Cre-lox or flp-frt sites in a recombination mediated cassette exchange (RMCE) approach; 3) linear, sequence-specific recombination (e.g., via a phage integrase such as λ or phiC31); and 4) sequence-specific circle integration. Exemplary site-specific and homologous recombination systems include, but are not limited to, Cre-loxP, Flp-FRT, att-Int (Gateway), Red/ET, RecA, and the like. These and other recombination systems are well-known to those of ordinary skill in the art and are described in the following references, which are incorporated by reference: Branda et al, Developmental Cell, 6: 7-28 (2004); Baer et al, Curr. Opin. Biotech., 12: 473-480 (2001); Sauer, Nucleic Acids Research, 24: 4608-4613 (1996); Yu et al, Proc. Natl. Acad. Sci., 97: 5978-5983 (2000); Lee et al, Genomics, 73: 56-65 (2001); Muyrers et al, EMBO Rep., 1: 239-243 (2000); Cheo et al, Genome Research, 14: 2111-2120 (2004); Missirlis et al, BMC Genomics, 7: 73 (2006); U.S. Pat. Nos. 6,509,156; 6,465,254; 6,720,140; 5,776,449; 5,888,732; and the like. Recombinases may be provided by expression of genes that may be carried by the host genome, or by an episome, such as a plasmid, or by one or more component polynucleotides of a precursor replacement genome. Preferably, expression of recombinases are under inducible control in order to minimize the occurrence of spurious or undesired recombination during the assembly process. Also, preferably, a host organism is selected that is free of recombination elements used in the replacement genome (or DNA circle) assembly process, or a selected organism is treated to remove or disable such elements to prevent spurious or unintended recombination reactions.

The assembly process of the invention includes successive steps of recombining in a host organism a new component polynucleotide of a replacement genome with component polynucleotides that have previously been assembled, and which constitute a precursor replacement genome. Such steps are carried out using conventional vectors and transformation techniques in conjunction with a recombination system, such as one of those indicated above. Typically, each such step includes substeps of transforming the host with a vector containing a new component polynucleotide operationally associated with one or more unique recombination elements, culturing transformed host organisms, and selecting host organisms containing recombinants, i.e., precursor replacement genomes that have successfully recombined with a new component polynucleotide to generate a successive precursor replacement genome (or a completed replacement genome), as the case may be. In some embodiments, multiple component, polynucleotides may be recombined with a precursor replacement genome in a single cycle, e.g. using the approach of Church et al, International patent publication WO 2006/055836, which is incorporated herein by reference.

In one aspect, assembly of component polynucleotides may be carried out with site-specific recombination, as illustrated in FIGS. 1A-1G. Site-specific recombination elements are selected and arranged in vectors to drive recombination reaction to the desired products. Sets of site-specific recombination elements are provided that (i) have substantially no cross reactivity with one another, and (ii) are oriented so that stable integration occurs in each step of the assembly process. As reviewed by Branda et al (cited above), for example, the λ integrase family of site-specific recombination elements, which include loxP and FRT, share a common mechanism of DNA recombination that involves strand cleavage, strand exchange, and ligation. Although distinct at the nucleotide level, loxP and FRT sites share an overall structure which includes two 13 basepair palindromic sequences, or inverted repeats, separated by an 8 basepair asymmetric core, or spacer, sequence. In the presence of two sites, recombinase monomers bound to the inverted repeats promote the formation of a synaptic complex and recombination between the two sites. Strand cleavage, exchange, and ligation occur within the spacers. Because of spacer asymmetry, strand exchange is possible only when target sites are connected by synapses in one orientation. Consequently, the relative orientation of target sites with respect to one another determines the outcome of recombination: Cre and Flp recombinases will excise a circular molecule from between two directly repeated target sites, integrate a circular molecule into a linear molecule each possessing a target site, invert the DNA between two inverted sites, and exchange sequences distal to target sites present on two linear molecules. Because insertion ordinarily leaves two identical sites in cis configuration, which are themselves substrates for recombination, stable insertions are difficult or impossible using two wild type sites. However, many recombinases, such as Cre and Flp, tolerate certain variations in their target sequences and effectively catalyze recombination only between certain subsets of the alternative sites. This property is exploited to permit successive recombination events for replacement genome assembly. Variant target sites for λ intergrase recombinases, such as Cre and Flp, fall into two classes: spacer variant and invert-repeat variants. The first class contains nucleotide substitutions within the spacer sequence and exploits the finding that it is spacer length, not sequence that is the critical factor for efficient recombination, so long as the sequence between participating sites is identical. Recombination is therefore efficiently mediated between pairs of homotypic (e.g. FRT/FRT or $F_3/F_3$) but not heterotypic (e.g. $FRT/F_3$) sites. The second class of alternative sites (inverted repeat variants) may also be exploited to provide stable insertions. A target site containing a nucleotide substitution in the "left side" inverted repeat (an "LE" mutant site) can recombine with a site containing an analogous substitution in the "right end" inverted repeat (an "RE" mutant site), although at a slower reaction rate than wild type sequences. Such mutants are designed so that the recombination product harbors one wild type site and one LE/RE double mutant site, the latter being effectively inert. Thus, insertion with such single mutant LE and RE sites results in the formation of only one potentially active recombination element, which itself may be inactivated or modified and used for subsequent insertions. These concepts are illustrated in FIGS. 1A-1G for several embodiments of the invention.

Figure 1A:
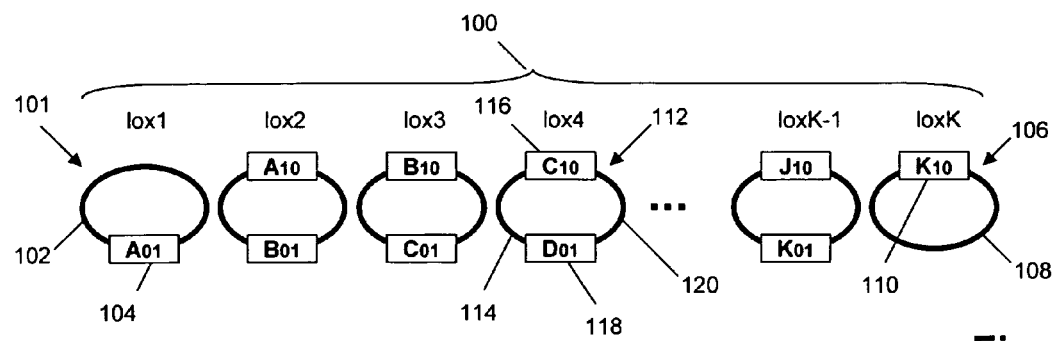
FIGS. 1A-1G illustrates schematically several methods of assembling in a host organism donor genome segments into a replacement genome.
Figure 1B:
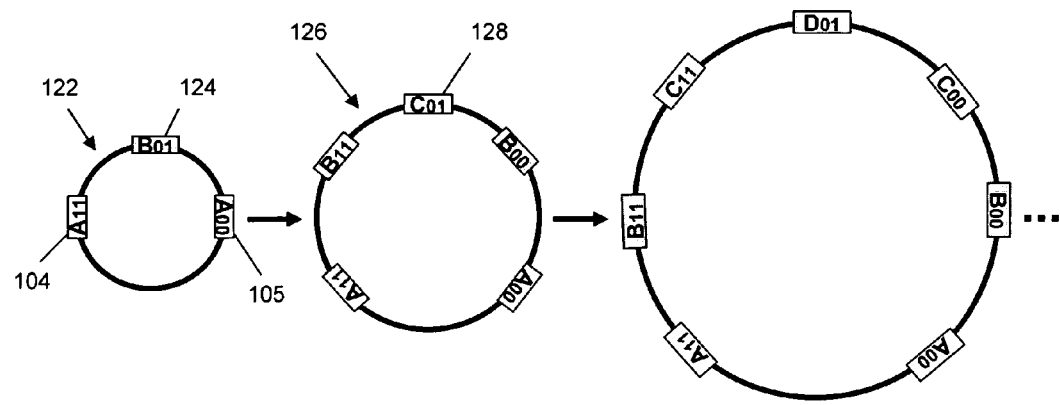
Figure 1C:
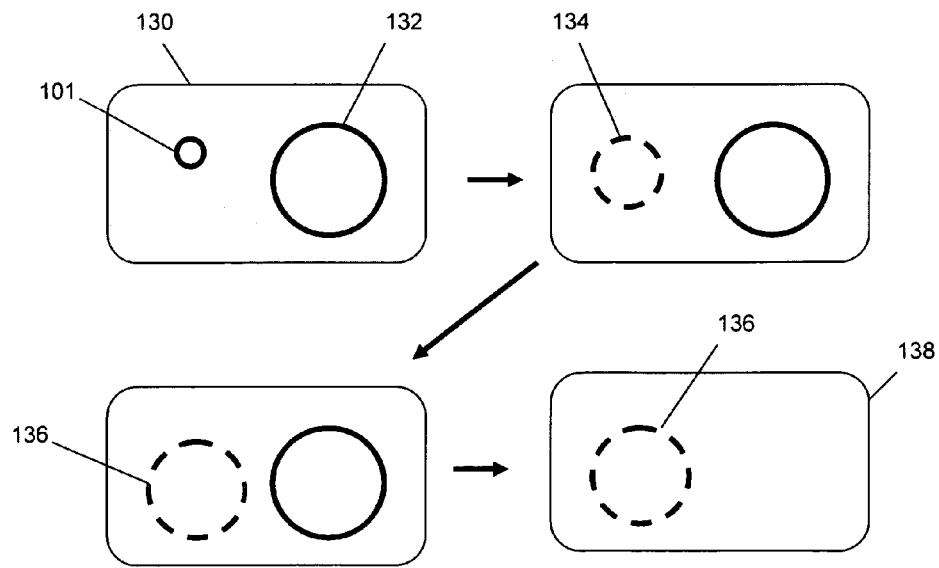

FIG. 1A illustrates a plurality of component polynucleotides (100) carried in vectors, lox1 through loxK, that each have a unique combination of site-specific recombination elements labeled "$A_{01}$," "$A_{10}$," "$B_{01}$," "$B_{10}$," "$C_{01}$," ... "$K_{10}$," where each different letter, "A," "B," etc., indicates a different non-cross-reacting site-specific recombination element (such as, mutant loxP sites of the invention), and where subscripts "01" and "10" indicate a recombination element has an RE mutant site ("01") or an LE mutant site ("10"). Correspondingly, a letter with subscripts "11" indicates a double mutant site and a letter with subscripts "00" indicates a mutant-free site. It is noted that the diagrams of vectors are only symbolic representations and are not to scale or proportion. For example, even though the site-specific recombination elements are shown at opposite sides of the vectors, this is not a required configuration. The recombination elements may be juxtaposed or they may be interspersed in the vector or component polynucleotide. Vector lox1 (101) containing initial component polynucleotide (102) requires only a single recombination element "$A_{01}$" (104) in this embodiment. Likewise, vector loxK (106) containing the final component polynucleotide (108) requires only a single recombination element "$K_{10}$" (110). Vectors lox2 through loxK-1 each have two different recombination elements, as exemplified by vector lox4 (112), which comprises component polynucleotide (114), recombination element "$C_{10}$" (116), recombination element "$D_{01}$" (118), and portion (120), which may be part of component polynucleotide (114) or simply a connection between the two recombination elements (e.g. a bond connecting two adjacent sequences or an intervening polynucleotide). In this embodiment, each of the component polynucleotides-containing vectors of plurality (100), except for the first (lox1) and the last (loxK), contains at least a first recombination element (e.g. "$A_{10}$" of lox2) in common with its immediately preceding vector (i.e. "$A_{01}$" of lox1) in the predetermined order shown and at least a second recombinant element (e.g. "$B_{01}$" of lox2) in common with its immediately succeeding vector (i.e. "$B_{10}$" of lox3), wherein such first and second recombination elements are different (i.e. in this embodiment, the first is type "A" and the second is type "B"). Again, an important property of the different types (or kinds) of recombination elements is that members or variants of one type (or kind) do not cross react (or substantially do not cross react) with members or variants of another type (or kind). As illustrated in FIG. 1B, component polynucleotides of plurality (100) are assembled stepwise by adding them one component polynucleotide at a time to form a succession of growing nucleic acid constructs (such as precursor replacement genomes). In one aspect, each step in the assembly process comprises a cycle of steps (or substeps) including transforming a host and selecting a resulting transformant using a selectable marker. The relative ordering of recombination elements is shown in first recombinant (122), which is the first precursor construct. Since site-specific recombination is conservative, in that DNA synthesis is not required and sequences are neither lost nor gained in the reaction, first recombinant (122) contains pieces of all the recombination elements of the two vectors that were combined, i.e. two copies of an "A" type recombination element in double mutant form (104) and in mutant-free form (105), and one copy of recombination element "$B_{01}$" (124), which serves as the unique recombination site for the next vector, lox3. After transformation, recombination and selection, the resulting host harboring first recombinant (122) is transformed with vector lox3 to form the next recombinant, or precursor construct (126). Again, sequences are conserved in the recombinant of (122) and lox3 so that precursor construct (126) contains five recombination elements: "$A_{00}$" (active), "$A_{11}$" (inert), "$B_{00}$" (active), "$B_{11}$" (inert), and "$C_{01}$" (128), which again is the unique recombination site for the next vector, lox4. The process continues until the desired nucleic acid construct is complete. The ordering of the active recombination elements ("$A_{00}$," "$B_{00}$," "$C_{00}$," etc.) relative to the inert recombination elements ("$A_{11}$," "$B_{11}$," "$C_{11}$," etc.) may be varied by changing the ordering of the LE and RE mutant sites in vectors (100). For example, if lox2 contained "$B_{10}$" and lox3 contained "$B_{01}$," then the positions of "$B_{11}$" and "$B_{00}$" would be swapped and the resulting vector corresponding to (126) would have inert site "$A_{11}$" sandwiched between "$A_{00}$" and "$B_{00}$.". As indicated, in this embodiment, recombination takes place in a host cell, such as illustrated diagrammatically in FIG. 1C. Host organism (130) is transformed by initial vector (101) to form a host containing a host genome (132) and vector (101). In subsequent cycles of the assembly process, successively larger recombinants (134), i.e. precursor constructs, are formed until a completed construct (136) is present, which may be a replacement genome. In such case, host genome (132) is then removed or ablated to produce synthetic cell (138) containing only replacement genome (136).

As discussed more fully below, the above process may be carried out with pairs of LE and RE mutant recombination elements for each type, "A" through "K," as taught by Missirlis et al, BMC Genomics, 7: 73 (4 Apr. 2006), which is incorporated by reference. Briefly, LE and RE mutant pairs are prepared for each type of recombination element. When a recombination event occurs (e.g., part of element "B10" on lox3 is combined with element "$B_{01}$" on lox3), both mutants are present in only one of the product sites, and the other product site is free of mutations. This results directly in a modular replacement genome. That is, the operable recombination sites may be used with the recombination system employed to exchange component polynucleotides for modifying the properties of the nucleic acid construct, e.g. using a RMCE procedure.

Figure 1D:
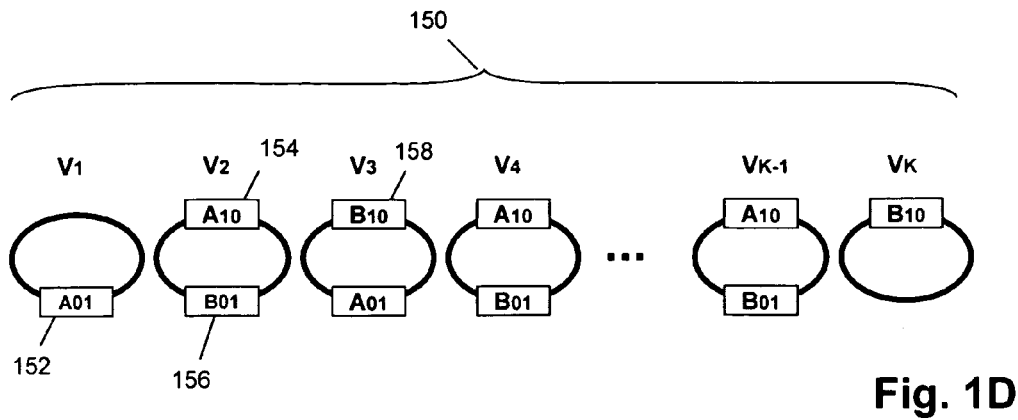
Figure 1E:
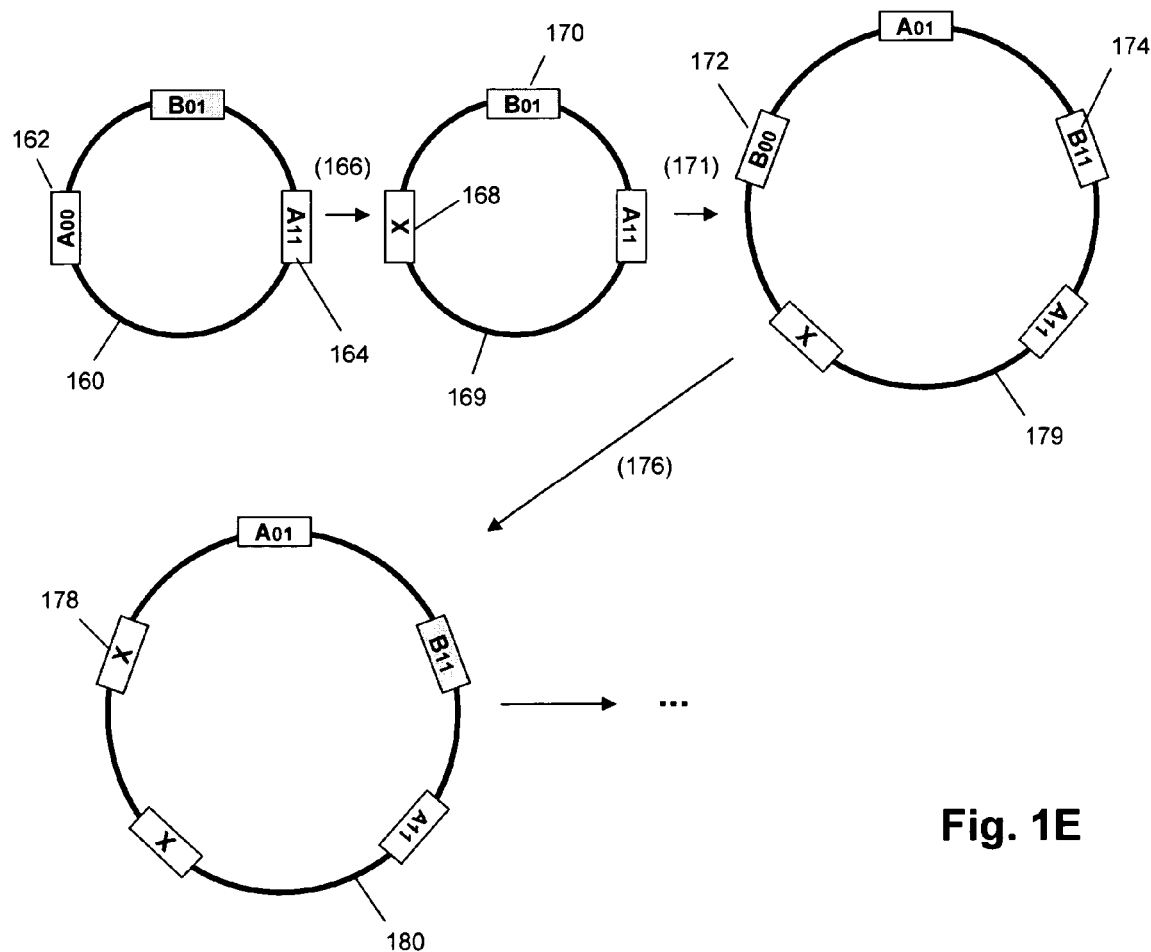

In another aspect, component polynucleotides may be assembled into a replacement genome by using fewer recombination elements, as illustrated in FIGS. 1D and 1E. A plurality of component polynucleotides is provided in vectors $V_1$ through $V_K$ (150). In this embodiment, the vectors do not each have one or more unique recombination elements; instead, the recombination elements are re-used in alternating cycles of component polynucleotide incorporation. Such re-cycling of recombination elements may be accomplished with a plurality of different types of recombination elements, each of which is provided as a pair of single mutants that may recombine with each other to produce an active mutant-free form and an inert double mutant form. Such a plurality of different recombination elements may contain, for example, two, three, four, five, six, seven, eight recombination elements, at least one of which is a mutant loxP element of the invention, or in another aspect, all of which are mutant loxP elements of the invention. In one aspect, recombination elements may be conveniently introduced into BACs carrying the component polynucleotides by Red/ET recombination, e.g. as disclosed in U.S. Pat. No. 6,509,156; and Yu et al, Proc. Natl. Acad. Sci., 97: 5978-5983 (2000); and/or using reagents commercially available from GeneBridges GmbH (Dresden, Germany). In particular, using appropriate host bacteria, sequences to be inserted into a BAC may be prepared by PCR, where the resulting amplicon contains unique flanking sequences of 30-50 basepairs. Such amplicons are recombined with regions of the BAC bounded by the same unique sequences.

In FIG. 1D, vector $V_1$ containing the first component polynucleotide and vector $V_K$ containing the last component polynucleotide, $V_K$, each have a single recombination element, and the rest of the vectors, $V_2$ through $V_{K-1}$, each have two. Recombination element $A_{01}$ (152) on $V_1$ is a single mutant site that is operable with recombination element $A_{10}$ (154) on $V_2$, which is a different single mutant site. Likewise, recombination element $B_{01}$ (156) on $V_2$ is a single mutant site that is operable with recombination element $B_{10}$ (158) on $V_3$, which is a different single mutant site. The same four sites may be used with all of the vectors $V_1$ through $V_K$, when used as follows. $V_1$ and $V_2$ are transformed into a Red/ET competent host that also expresses an appropriate recombinase to form recombinant (160), in which recombination elements $A_{01}$ ($V_1$) and $A_{10}$ ($V_2$) are changed to functional $A_{00}$ site (162) and non-functional $A_{11}$ site (164). An amplicon is prepared containing 30-50 basepair flanking sequences that are identical to sequences flanking $A_{00}$ (162) on recombinant (160). The host bacteria containing recombinant (160) is transformed with the amplicon so that it can recombine (166) with the portion of recombinant (160) containing $A_{00}$ (162) to produce recombinant (169), which is shown to have a disabled recombination site "X" (168). An advantage of the Red/ET system is that recombinants can be detected by PCR; growth on a selective medium is not required. Modified recombinant (169) may then be used in the next assembly step by transforming its host with vector $V_3$ containing a third component polynucleotide and recombination elements $B_{10}$ and $A_{01}$ to form (171) recombinant (179), which contains a functional $B_{00}$ site and a non-functional $B_{11}$ site. As above, after selection of a recombinant (179), the functional $B_{00}$ site is disrupted (176) to form modified recombinant (or precursor construct) (180). Assembly of a desired nucleic acid construct continues in a similar manner for the remaining component polynucleotides.

Figure 1F:
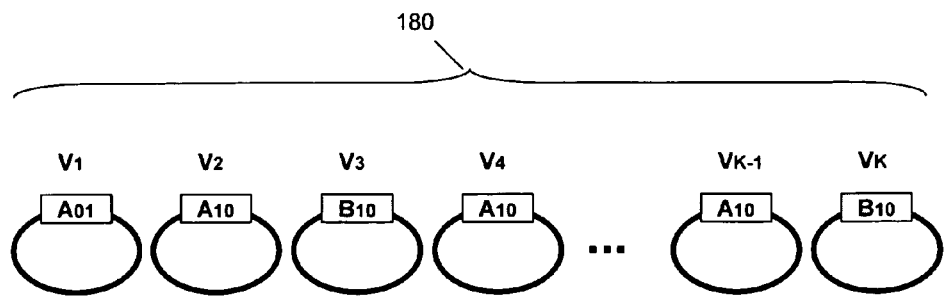
Figure 1G:
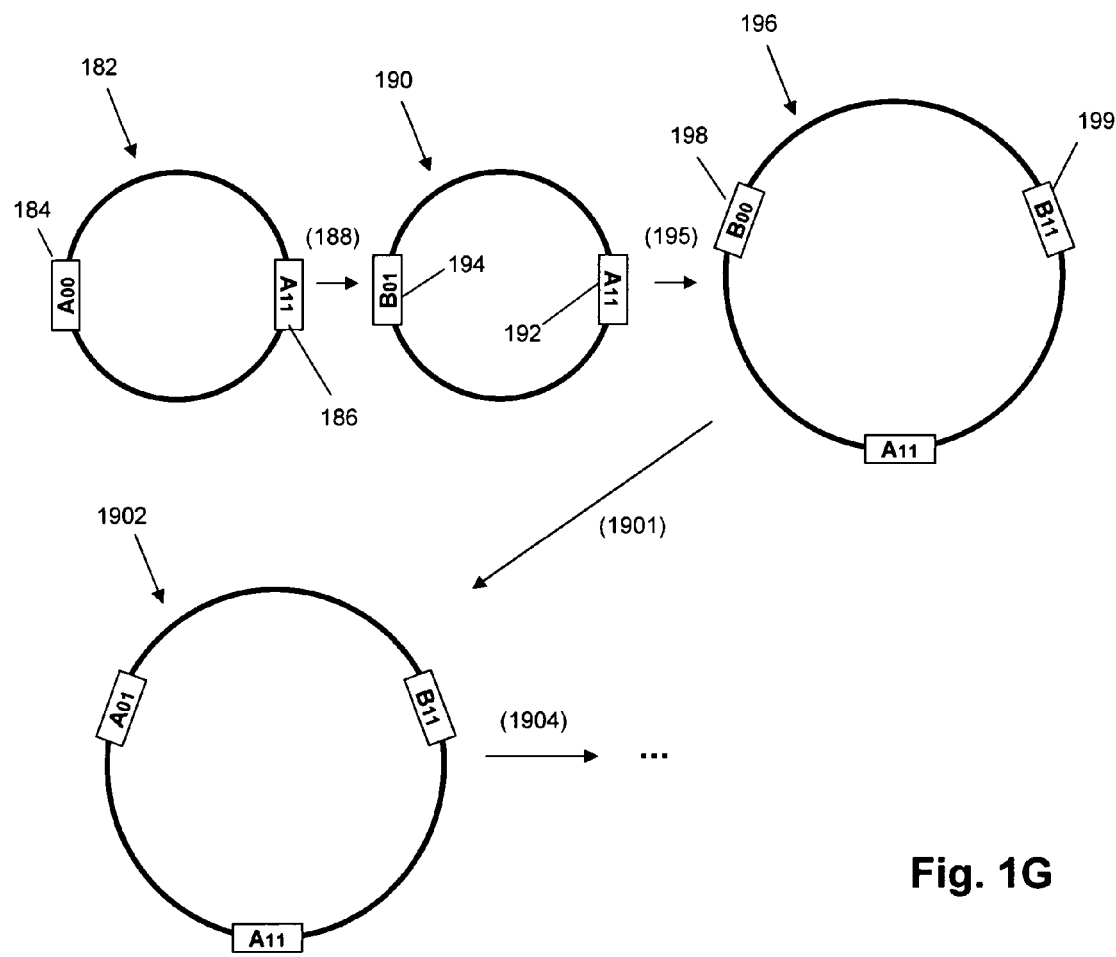

A recombination system, such as Red/ET may also be used as illustrated in FIGS. 1F-1G to modify an undesired functional recombination element within a polynucleotide-addition cycle. A plurality of vectors (180) is provided that each contains only one single mutant form of one type of recombination element. As above, only two types recombination elements are shown in the embodiment of FIG. 1F (A's and B's); however, further types of recombination elements may be employed in alternative embodiments. As above, at least one of the types of recombination elements may be a mutant loxP site of the invention, or all of the different types of recombination elements may be different mutant loxP sites of the invention. Vectors $V_1$ and $V_2$ are recombined to form recombinant (182) that contains active recombination element $A_{00}$ (184) and inert recombination element $A_{11}$ (186). In this embodiment, instead of inactivating element $A_{00}$, a homologous recombination system, such as Red/ET, is employed to exchange the active recombination element $A_{00}$ with a recombination element complementary to the element of the next vector to be inserted. (As above, this allows the type A recombination elements to be re-used in subsequent steps). After such exchange (188), precursor construct (190) is formed that has one inactive recombination element $A_{11}$ (192) and one active recombination element $B_{01}$ (194). Precursor construct (190) is then combined with vector $V_3$ so that element $B_{01}$ recombines (195) with element $B_{10}$ of vector $V_3$ to form precursor construct (196) containing active $B_{00}$ (198) and inert $B_{11}$ (199). In the next step, $B_{00}$ is exchanged (1901) with $A_{01}$ to produce precursor construct (1902). Similar cycles (1904) of transforming to add a component polynucleotide and transforming to exchange a recombination element are carried out until a final nucleic acid construct is assembled.

As mentioned above, mutant loxP sequences of the invention enable the stepwise assembly of a plurality of polynucleotides to form a nucleic acid construct inside of a host cell. In a particular embodiment, such assembly permits the construction of nucleic acid constructs that are larger than the expected size of single molecules of DNA that can be conventionally handled. For example, DNA, such as genomic DNA, that is handled by conventional laboratory operations, such as, pipetting, mixing, stirring, transforming, and the like, typically is broken into fragments less than about 250 kb-300 kb by shearing forces created by such operations. Thus, in one aspect, mutant loxP sequences of the invention permit the assembly in a host organism of nucleic acid constructs having a size of greater than 400 kilobases (kb), or greater than 500 kb, or greater than 600 kb, or greater than 700 kb.

Typically, component polynucleotides used in assembling a nucleic acid construct are cloned using conventional techniques in conventional cloning vectors, including plasmids, phages, cosmids, and/or bacterial artificial chromosomes (BACs) and P1-derived artificial chromosomes (PACs), P1 vectors, and the like. In one aspect, in order to minimize assembly steps, component polynucleotides may be provided as inserts of large-insert cloning vectors, such as BACs or PACs. A large-insert vector is a vector capable containing an insert having a length in the range of from 50 kb to 300 kb, or greater, and transforming a prokaryotic host organism, such as a bacteria. In particular, a large number of BACs are available for use in RecA E. coli host organisms. In one aspect, component polynucleotides are cloned in BAC vectors, which are described in the following references that are incorporated by reference: Zhao et al, editors, Bacterial Artificial Chromosomes (Humana Press, Totowa, N.J., 2004); Kim et al, Genomics, 34: 213-218 (1996); Shizuya et al, Proc. Natl. Acad. Sci., 89: 8794-8797 (1992); U.S. Pat. Nos. 5,874,259 and 6,472,177; and the like. Techniques for assembling inserts into BACs from several smaller pieces are well known in the art, as evidenced by the following reference: O'Connor et al, Science, 1307-1312 (1989), which is incorporated by reference. Exemplary vectors that may be used with the invention, with no or minor modifications, include pBeloBAC11, pBACe3.6, pCC1BAC, pSMARTVC, pIndigoBAC-5, SuperCos 1, and the like, which are commercially available or described in GenBank.

Figure 3:
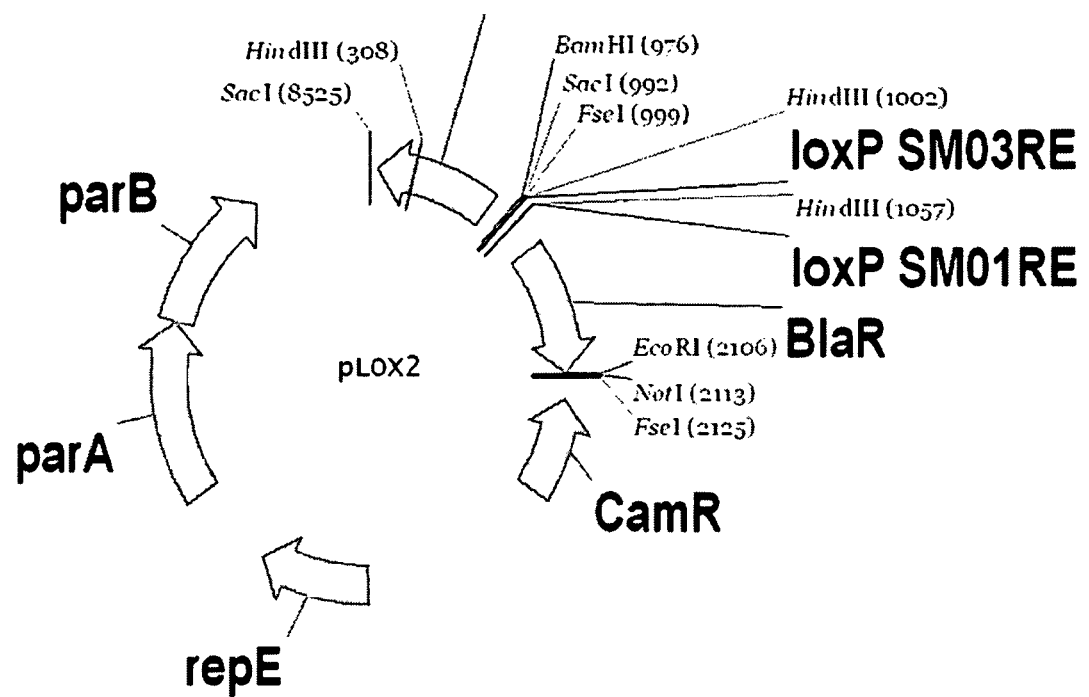
FIG. 3 is a genetic map of a vector incorporating loxP recombination elements for incorporating donor genome segments into a growing precursor replacement genome.

FIG. 3 is a genetic map of a representative pLOX vector that may be used for maintaining a plurality of component polynucleotides for assembly into a replacement genome. Each vector has mutant loxP site for integration with a precursor replacement genome, and a recipient lox P site for receiving the next incoming clone in a subsequent assembly step. The replicon region of the vector is removed by Fse1 digestion prior to transformation.

Generally, and in the particular examples above, transforming host microorganisms with vectors carrying component polynucleotides is carried out with conventional techniques. As used herein, the terms "transformation" and "transfection" are intended to refer to a variety of art-recognized techniques for introducing an exogenous nucleic acid sequence (e.g., DNA) into a host cell, including calcium phosphate or calcium chloride co-precipitation, DEAB-dextran-mediated transfection, lipofection, electroporation, optoporation, mechanical injection, biolistic injection, and the like. Suitable methods for transforming or transfecting host cells are found in Sambrook, et al. (Molecular Cloning: A Laboratory Manual. 2nd, ed., Cold Spring Harbor Laboratory, Cold Spring Harbor Laboratory Press, Cold Spring Harbor, N.Y., 1989), and like laboratory manuals.

Transformed microorganisms, that is, those containing recombinant molecules, may be selected with a variety of positive and/or negative selection methods or markers. In certain aspects, the positive selection marker is a gene that allows growth in the absence of an essential nutrient, such as an amino acid. For example, in the absence of thymine and thymidine, cells expressing the thyA gene survive, while cells not expressing this gene do not. A variety of suitable positive/negative selection pairs are available in the art. For example, various amino acid analogs known in the art could be used as a negative selection, while growth on minimal media (relative to the amino acid analog) could be used as a positive selection. Visually detectable markers are also suitable for use in the present invention, and may be positively and negatively selected and/or screened using technologies such as fluorescence activated cell sorting (FACS) or microfluidics. Examples of detectable markers include various enzymes, prosthetic groups, fluorescent markers, luminescent markers, bioluminescent markers, and the like. Examples of suitable fluorescent proteins include, but are not limited to, yellow fluorescent protein (YFP), green fluorescence protein (GFP), cyan fluorescence protein (CFP), umbelliferone, fluorescein, fluorescein isothiocyanate, rhodamine, dichiorotriaziny-lamine fluorescein, dansyl chloride, phycoerythrin and the like. Examples of suitable bioluminescent markers include, but are not limited to, luciferase (e.g., bacterial, firefly, click beetle and the like), luciferin, aequorin and the like. Examples of suitable enzyme systems having visually detectable signals include, but are not limited to, galactosidases, glucorinidases, phosphatases, peroxidases, cholinesterases and the like. In other aspects, the positive selection marker is a gene that confers resistance to a compound which would be lethal to the cell in the absence of the gene. For example, a cell expressing an antibiotic resistance gene would survive in the presence of an antibiotic, while a cell lacking the gene would not. For instance, the presence of a tetracycline resistance gene could be positively selected for in the presence of tetracycline, and negatively selected against in the presence of fusaric acid. Suitable antibiotic resistance genes include, but are not limited to, genes such as ampicillin-resistance gene, neomycin-resistance gene, blasticidin-resistance gene, hygromycin-resistance gene, puromycin-resistance gene, chloramphenicol-resistance gene and the like. In certain aspects, the negative selection marker is a gene that is lethal to the target cell in the presence of a particular substrate. For example, the thyA gene is lethal in the presence of trimethoprim. Accordingly, cells that grow in the presence trimethoprim do not express the thyA gene. Negative selection markers include, but are not limited to, genes such as thyA, sacB, gnd, gapC, zwJ, talA, taiB, ppc, gdhA, pgi, Jbp, pykA, cit, acs, edd, icdA, groEL, secA and the like.

Selection methods and/or markers may be used efficiently in a multi-step assembly process, such as called for by the invention, by employing a pair of selection methods or markers that are switched, or used reciprocally, between successive recombination steps, e.g. as taught by O'Connor et al, Science, 244: 1307-1312 (1989); Kodumal et al, Proc. Natl. Acad. Sci., 101: 15573-15578 (2004); or the like.

Screening for Functional Mutant LoxP Sequences

Synthetic loxP oligonucleotides were created that contained a combination of inverted repeat mutations (the lox66 and lox71 mutations) and mutant spacer sequences, degenerate at 6 of the 8 positions. After in vitro Cre recombination, 3,124 recombinant clones were identified by sequencing. Table II lists novel mutant loxP spacer regions discovered. Table III lists novel pairs of mutant loxP spacers associated with successful recombination reactions. Table IV lists novel pairs of non-self recombining mutant loxP spacers. That is, Table IV list mutant loxP spacer pairs whose member loxP recombination elements do not react with elements identical with themselves, but do react with their non-identical pair. Included in these sets are 31 unique, novel, self-recombining sequences. 12 spacer sets with restricted promiscuity were also identified. It was observed that increased guanine content at all spacer positions save for position 8 resulted in increased recombination. It was also observed that recombination between identical spacers was not preferred over non-identical spacers. A set of 16 pairs of loxP spacers was identified that reacted at least twice with another spacer, but not themselves. Neither the wild-type P1 phage loxP sequence nor any of the known loxP spacer mutants appeared to be kinetically favored by Cre recombinase.

Figure 4A:
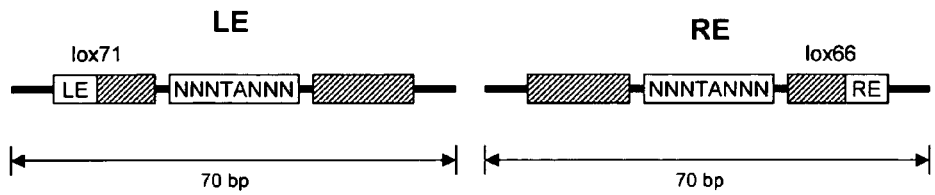
FIGS. 4A-4C show a diagram of the scheme used to screen for mutant loxP spacer sequences.
Figure 4A:
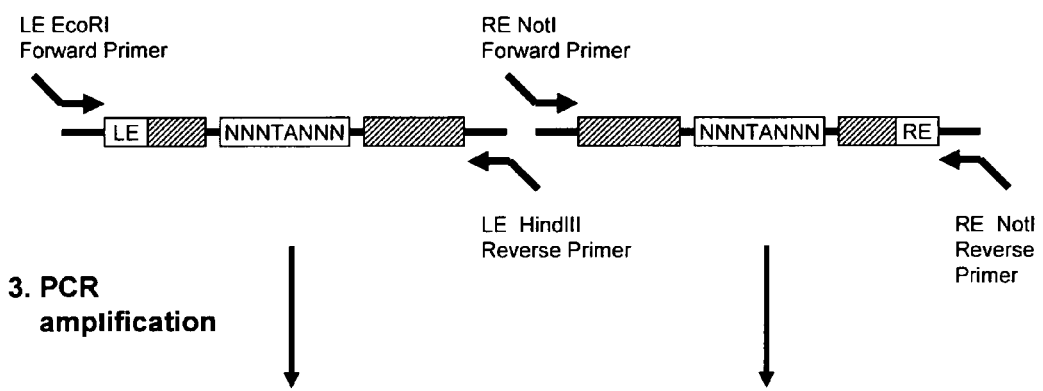
Figure 4A:
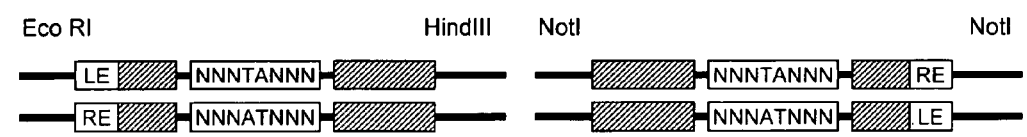
Figure 4A:
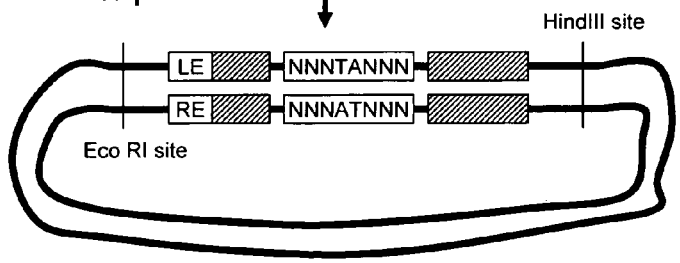
Figure 4B:
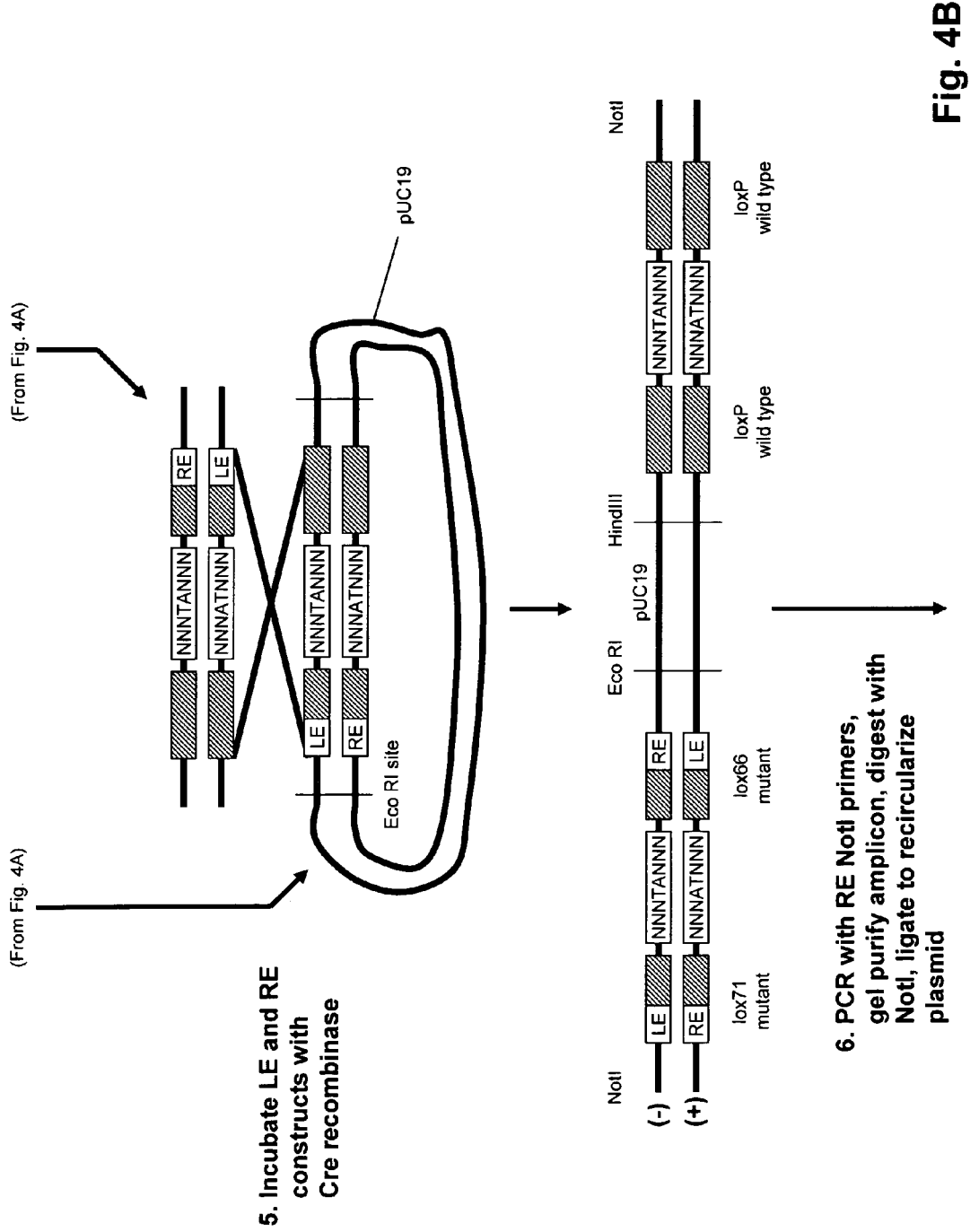
Figure 4C:
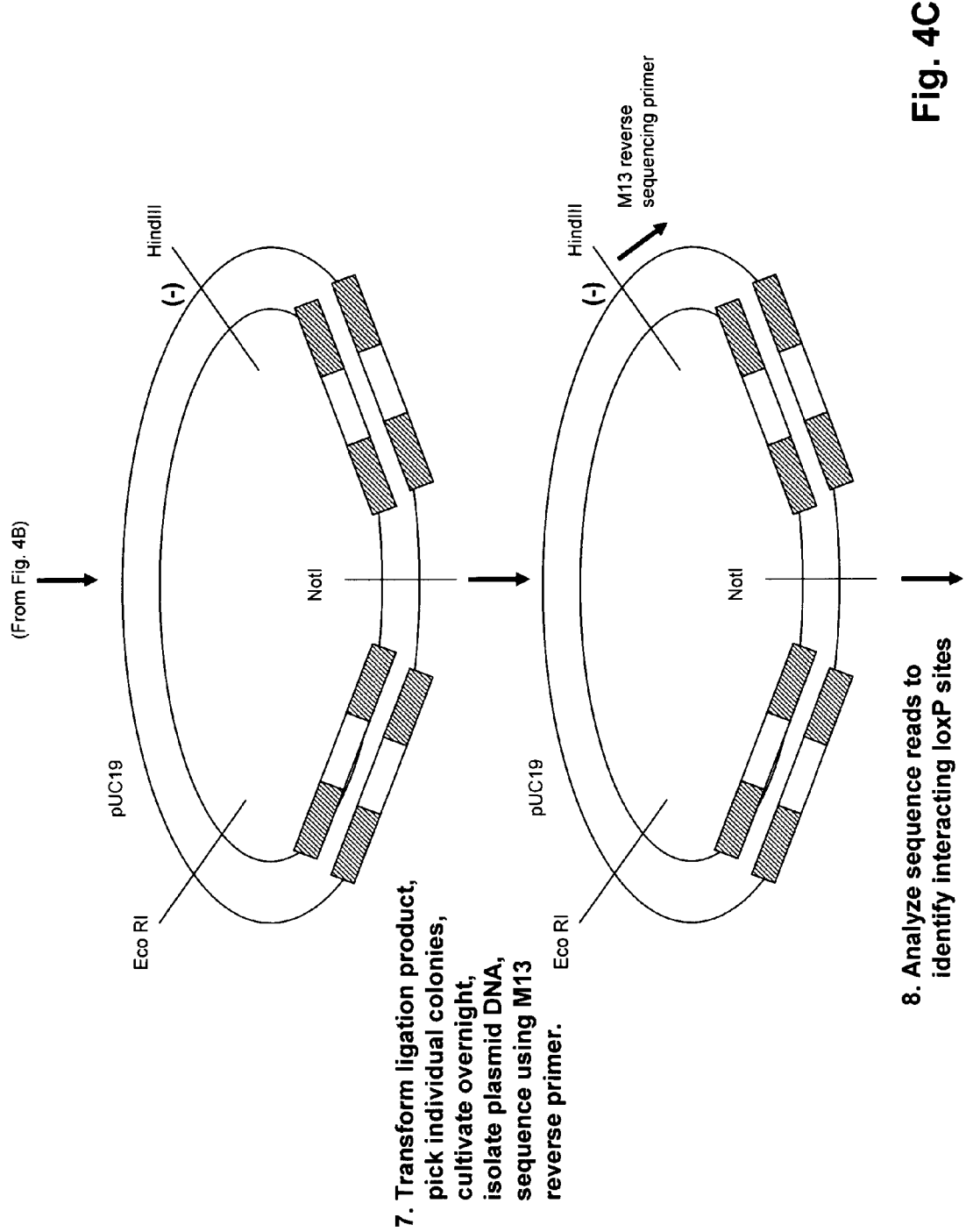

The recombination reaction. Two oligonucleotides (LE, RE) were designed that contained loxP sites with six degenerate spacer nucleotides (positions 1, 2, 3, 6, 7, 8) and two central fixed spacer nucleotides (4 and 5) (FIGS. 4A-4C). The central nucleotides in the 4 and 5 positions were limited to thymine and adenine residues because these have been previously suggested by mutational analysis to be essential for strand exchange. One of the oligonucleotide pools (LE) contained the lox71 left arm mutant sequence and the other (RE) contained the lox66 right arm mutant sequence. These oligonucleotides were converted to double stranded products by PCR. Primers used to generate the LE PCR product were tailed with EcoRI and HindIII restriction sites for subcloning into the pUC19 vector and primers used to generate the RE PCR product were tailed with NotI restriction sites. These two pools of oligonucleotides were then incubated in the presence of Cre recombinase as illustrated in FIGS. 4A-4C. A 20 μL in vitro recombination reaction was set up with approximately 300 ng of supercoiled LE/pUC19 plasmid, 30 ng of double stranded RE PCR product, 200 ng of CRE Recombinase (BD Bioscience) and 1× (final concentration) Cre Recombinase Buffer (BD Biosciences). The reaction was incubated overnight at room temperature and the desired 1.8 kbp recombination products were agarose gel purified and amplified by PCR using the RE_NotI_Forward and RE_NotI_Reverse primers, disclosed in Missirlis et al (cited above).

Sequencing and analyzing the successful recombinants. After PCR amplification, the recombination products were digested with NotI, purified on an agarose gel, and re-circularized with T4 DNA ligase to generate a library of paired loxP recombination products in pUC19. These plasmids were transformed into DH10B cells, grown overnight, and plated on solid media. Each individual colony (clone) represented a distinct, successful, recombination reaction between two loxP spacer sequences. A total of 5,670 clones were picked, grown overnight, and plasmid DNA was isolated and sequenced with M13 reverse sequencing primer using conventional techniques. Of these clones, 4,992 yielded successful sequence.

According to the reaction mechanism, wild-type inverted repeats flanking one spacer and the lox66 and lox71 inverted repeats flanking the other spacer were expected in the post-recombination sequences. Consequently, a typical sequencing read was composed of the following sequence features (median feature location from read start given in bp): left wild-type inverted repeat (14 bp), first spacer (27 bp), right wild-type inverted repeat (34 bp), NotI site (65 bp), lox71 inverted repeat mutant (91 bp), second 8 bp spacer (104 bp), lox 66 inverted repeat mutant (111 bp), start of the pUC19 vector (133 bp) and EcoRI site (143 bp). Successful recombination reactions were defined as those sequences that contained exact matches to the wild-type inverted repeat sequences flanking an 8 bp spacer (ATTACTTCGTATA NNNNNNNN TATACGAAGTTAT) and the lox66, lox71 inverted repeat mutations flanking an 8 bp spacer (TACCGTTCGTATA NNNNNNNN TATACGAACGGTA). Five spacers lacked the central TA nucleotides but were retained in the analysis because they successfully recombined.

There were 3,124 reverse strand sequence reads from successful recombination reactions that were used for further analysis. However, these sequences could not be analyzed as is. First, each spacer was reverse complemented to facilitate comparisons with published loxP spacers as most spacers are published in the positive strand orientation. Since each sequence read represented the final product of recombination, the spacer sequence of the original input LE and RE oligonucleotides had to be inferred based on the published location of the scissile bonds and mechanism of recombination, illustrated in FIG. 2. For each recombination reaction, the input LE oligonucleotide spacer was defined as loxP spacer position 1 from the LE/RE double inverted repeat mutant and positions 2-8 from the spacer with wild-type inverted repeats. Accordingly, the input RE oligonucleotide spacer was defined as position 1 from the wild-type inverted repeat loxP spacer sequence and positions 2-8 of the LE/RE double inverted repeat mutant.

Each recombinant DNA molecule derived from mismatching spacers gave rise to two pools of PCR products from the same PCR reaction (FIG. 4A-4C, steps 5 & 6), one pool derived from amplification of the positive strand of the initial recombinant molecule and another from the negative strand. From each of these two types of PCR products the top, or positive strand was sequenced. The sequence of input oligonucleotides was inferred using the established loxP recombination mechanism. Four categories of inferred input oligonucleotides were established based on the location of the mismatched base(s). The Type I class corresponded to identical spacers in the two input oligonucleotides that yielded a recombinant molecule with identical spacers. For this class, the PCR products and sequence reads originating from the positive versus negative strand of the original recombinant molecule were identical. The Type II class corresponded to input oligonucleotides with discrepancies in positions 1 and/or 8 in their reacting spacers. For this class the input oligonucleotides can be unambiguously assigned as well because positions 1 and 8 are not exchanged between strands during recombination. The Type III class corresponded to input oligonucleotides with one or more mismatches in positions 2 through 7, which are the bases that undergo strand exchange during recombination. For Type III, the sequence of the input spacers could be inferred but the origin within the LE or RE oligonucleotides was ambiguous. Lastly, the Type IV class corresponded to input oligonucleotides that had mismatches in positions 1 or 8, and also had one or more mismatches in positions 2 through 7. For this class the precise identity of the input oligonucleotides was ambiguous because two different pairs of oligonucleotides could produce the same PCR products and sequence reads.

As a result of this analysis the following Type I, II, and III sequences of Table II (set forth below) were determined to correspond to novel mutant loxP sequences useful for carrying out site-specific recombination reactions.

Each sequence read had two, usually non-identical, loxP spacers representing a distinct recombination reaction. Thus, each spacer in the library of Type I, II, and III sequences had a promiscuity profile defined by the number and kind of loxP sites with which it recombined. Inferred spacer sequences were further divided into two sets: self (a spacer sequence that recombined with itself plus one or more other spacer sequences) and non-self (a spacer sequence that did not recombine with itself, but did recombine with another non-self spacer more than once). The majority of spacer pairs found were singleton non-self spacer pairs. The self and non-self sets are mutually exclusive. In the set of 3,124 successful recombination reactions, 32 self-recombining spacers were discovered. Of these, only one spacer AGGTATGC or lox23 has been described previously, the remaining 31 (Table III) are novel self-recombining spacers. Spacers TTTTAGGT and GGCTATAG recombined solely with themselves but this exclusivity may be a reflection of limited sampling rather than a property of the spacer.

Selecting candidate spacers for serial site-specific recombination. Traditionally candidate loxP spacer sequences with the greatest potential utility for genetic engineering will self-recombine and exhibit limited promiscuity. Some promiscuity is tolerable if the sites prone to interaction are used in constructs in a mutually exclusive manner. We visualized self and non-self spacer interactions as a network using Cytoscape (Shannon et al, Genome Research, 13: 2498-2504 (2003)) in order to identify spacer cross-reactivity. Based on the degree of cross-reactivity with other sequences, the following 11 self and 1 non-self non-promiscuous spacers were selected (the number in parentheses is the number of other self-recombining partners): GTATAGTA (0), GGCTATAG (0), TCGTAGGC (2), GCGTATGT (2), TTGTATGG (1), GGATAGTA (1), GTGTATTT (1), AGGTATGC (1), GGTTACGG (1), TTTTAGGT (1), and GAGTACGC (1) and [GTGTACGC (2) and GTGTACGG (2)] (non-self set).

KITS OF THE INVENTION

In one aspect, kits of the invention comprise one or more oligonucleotides of the following form:

$LE_1$-$S_1$-$RE_1$ where: $LE_1$ is a mutant or wild type left inverted repeat of a loxP recombination element and $RE_1$ is a mutant or wild type right inverted repeat of a loxP recombination element such that whenever $LE_1$ is a wild type sequence, $RE_1$ is a mutant sequence, and whenever $LE_1$ is a mutant sequence, $RE_1$ is a wild type sequence; and $S_1$ is a mutant loxP spacer regions selected from the group listed in Table II. Such one or more oligonucleotides of the kits may be provided in double stranded form, which may be imbedded in larger oligonucleotides that have ends with primer binding sites for convenient amplification, or that have ends ready for insertion into nucleic acid constructs, e.g. "sticky" ends corresponding to ends produced by conventional restriction endonuclease cleavage. Alternatively, such oligonucleotides may be provided as inserts of conventional vectors. In additional embodiments, such kits may further include reagents for inserting recombinant elements of the kit into genomes of target organisms, either by restriction endonuclease digestion and ligations, or by homologous or site-specific recombinations, e.g. by a Red/ET recombination system, or like system. Kits may also include plasmids carrying genes encoding a Cre recombinase along with regulatory elements to permit the inducible expression of the Cre recombinase to permit user control over the timing of a desired recombination reaction.

In another aspect, kits of the invention comprise at leas one pair of oligonucleotides defined as follows: a first member of a pair is defined by the formula:

$$LE_1\text{-}S_1\text{-}RE_1$$

and a second member of the pair is defined by the formula:

$$LE_2\text{-}S_2\text{-}RE_2$$

where: $LE_1$ is a mutant or wild type left inverted repeat of a loxP recombination element and $RE_1$ is a mutant or wild type right inverted repeat of a loxP recombination element such that whenever $LE_1$ is a wild type sequence, $RE_1$ is a mutant sequence, and whenever $LE_1$ is a mutant sequence, $RE_1$ is a wild type sequence; $LE_2$ is a mutant or wild type left inverted repeat of a loxP recombination element and $RE_2$ is a mutant or wild type right inverted repeat of a loxP recombination element such that whenever $LE_2$ is a wild type sequence, $RE_2$ is a mutant sequence, and whenever $LE_2$ is a mutant sequence, $RE_2$ is a wild type sequence: with the proviso that whenever $LE_1$ is a mutant sequence, then $LE_2$ is a wild type sequence; and $S_1$ and $S_2$ within a pair arc either have the same sequence that is selected from the group consisting of:

GTATAGTA, GGCTATAG, TCGTAGGC, GTGTATTT, GTGTACGC,

CCCTATGT, TTGTATGG, GGATAGTA, AGGTATGC, GGTTACGG,

TTTTAGGT, GAGTACGC, and GTGTACGC, or, $S_1$ is GTGTACGC whenever $S_2$ is GTGTACGG; and $S_2$ is GTGTACGC whenever $S_1$ is GTGTACGG.

In another aspect, kits of the invention comprise a plurality of vectors for accepting component polynucleotides as inserts, each vector comprising a recombination element, such that at least one of such elements is a mutant loxP site of the invention. Vectors for use with methods of the invention may each further include one or more selectable markers for determining the presence of a recombinant molecule. Kits of the invention may further include one or more recombinases to catalyze recombination reactions involving recombination elements in the vectors of the kits. In one embodiment, kits of the invention include at least one Cre recombinase. In such aspect of the invention, different vectors of a kit have different recombination elements selected from recombination elements of the form:

$$LE_1\text{-}S_1\text{-}RE_1$$

where: $LE_1$ is a mutant or wild type left inverted repeat of a loxP recombination element and $RE_1$ is a mutant or wild type right inverted repeat of a loxP recombination element such that whenever $LE_1$ is a wild type sequence, $RE_1$ is a mutant sequence, and whenever $LE_1$ is a mutant sequence, $RE_1$ is a wild type sequence; and S is a mutant loxP spacer regions selected from the group listed in Table II. In another embodiment of this aspect of the invention, different recombination elements have the form as described above, but have spacer regions selected from the group consisting of:

TTTTAGGT, GGCTATAG, TCGTAGGC, GGTTACGG, GGATAGTA,

GCGTATGT, GTATAGTA, GCATAGGC, GTGTATTT, GTGTAGTC,

GTGTAGGA, TTGTATGG, GGGTAGCG, GGGTATTC, GAGTACGC,

GGTTAGGC, TGGTATGT, GGGTAGAC, TGGTAGTT, TGGTATGC,

CGGTAGGG, GGGTAGAT, GGGTAGGT, GGGTAAGC, GGGTAGTT,

GTGTAGGC, TGGTAGGG, GTGTAGGG, GGGTAGGT, GGGTAGGG, and GGGTAGGC.

In still another embodiment of this aspect of the invention, different recombination elements have the form as described above, but have spacer regions selected from the group consisting of:

GTATAGTA, GGCTATAG, TCGTAGGC, GTGTATTT, GTGTACGG,

GCGTATGT, TTGTATGG, GGATAGTA, AGGTATGC, GGTTACGG,

TTTTAGGT, GAGTACGC, and GTGTACGC.

Kits of the invention also include any delivery system for delivering materials or reagents for carrying out a method of the invention. In the context of recombination reactions for assembling a nucleic acid construct, such delivery systems include systems that allow for the storage, transport, or delivery of reaction reagents (e.g., vectors, enzymes, etc. in die appropriate containers) and/or supporting materials (e.g., buffers, written instructions for performing the reactions etc.) from one location to another. For example, kits include one or more enclosures (e.g., boxes) containing the relevant reaction reagents and/or supporting materials. Such contents may be delivered to the intended recipient together or separately. For example, a first container may contain an enzyme for use in a reaction, while a second container contains vectors.

DEFINITIONS

Terms and symbols of nucleic acid chemistry, biochemistry, genetics, and molecular biology used herein follow those of standard treatises and texts in the field, e.g. Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); and the like.

"Amplicon" means the product of a polynucleotide amplification reaction. That is, it is a population of polynucleotides, usually double stranded, that are replicated from one or more starting sequences. The one or more starting sequences may be one or more copies of the same sequence, or it may be a mixture of different sequences. Amplicons may be produced by a variety of amplification reactions whose products are multiple replicates of one or more target nucleic acids. Generally, amplification reactions producing amplicons are "template-driven" in that base pairing of reactants, either nucleotides or oligonucleotides, have complements in a template polynucleotide that are required for the creation of reaction products. In one aspect, template-driven reactions are primer extensions with a nucleic acid polymerase or oligonucleotide ligations with a nucleic acid ligase. Such reactions include, but are not limited to, polymerase chain reactions (PCRs), linear polymerase reactions, nucleic acid sequence-based amplification (NASBAs), rolling circle amplifications, and the like, disclosed in the following references that are incorporated herein by reference: Mullis et al, U.S. Pat. Nos. 4,683,195; 4,965,188; 4,683,202; 4,800,159 (PCR); Gelfand et al, U.S. Pat. No. 5,210,015 (real-time PCR with "taqman" probes); Wittwer et al, U.S. Pat. No. 6,174,670; Kacian et al, U.S. Pat. No. 5,399,491 ("NASBA"); Lizardi, U.S. Pat. No. 5,854,033; Aono et al, Japanese patent publ. JP 4-262799 (rolling circle amplification); and the like. In one aspect, amplicons of the invention are produced by PCRs. An amplification reaction may be a "real-time" amplification if a detection chemistry is available that permits a reaction product to be measured as the amplification reaction progresses, e.g. "real-time PCR" described below, or "real-time NASBA" as described in Leone et al, Nucleic Acids Research, 26: 2150-2155 (1998), and like references. As used herein, the term "amplifying" means performing an amplification reaction. A "reaction mixture" means a solution containing all the necessary reactants for performing a reaction, which may include, but not be limited to, buffering agents to maintain pH at a selected level during a reaction, salts, co-factors, scavengers, and the like.

"Duplex" means at least two oligonucleotides and/or polynucleotides that are fully or partially complementary undergo Watson-Crick type base pairing among all or most of their nucleotides so that a stable complex is formed. The terms "annealing" and "hybridization" are used interchangeably to mean the formation of a stable duplex. In one aspect, stable duplex means that a duplex structure is not destroyed by a stringent wash, e.g. conditions including temperature of about 5° C. less that the $T_m$ of a strand of the duplex and low monovalent salt concentration, e.g. less than 0.2 M, or less than 0.1 M. "Perfectly matched" in reference to a duplex means that the poly- or oligonucleotide strands making up the duplex form a double stranded structure with one another such that every nucleotide in each strand undergoes Watson-Crick basepairing with a nucleotide in the other strand. The term "duplex" comprehends the pairing of nucleoside analogs, such as deoxyinosine, nucleosides with 2-aminopurine bases, PNAs, and the like, that may be employed. A "mismatch" in a duplex between two oligonucleotides or polynucleotides means that a pair of nucleotides in the duplex fails to undergo Watson-Crick bonding.

"Hybridization" refers to the process in which two single-stranded polynucleotides bind non-covalently to form a stable double-stranded polynucleotide. The term "hybridization" may also refer to triple-stranded hybridization. The resulting (usually) double-stranded polynucleotide is a "hybrid" or "duplex." "Hybridization conditions" will typically include salt concentrations of less than about 1M, more usually less than about 500 mM and less than about 200 mM. Hybridization temperatures can be as low as 5° C., but are typically greater than 22° C., more typically greater than about 30° C., and preferably in excess of about 37° C. Hybridizations are usually performed under stringent conditions, i.e. conditions under which a probe will hybridize to its target subsequence. Stringent conditions are sequence-dependent and are different in different circumstances. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone. Generally, stringent conditions are selected to be about 5° C. lower than the $T_m$ for the specific sequence at s defined ionic strength and pH. Exemplary stringent conditions include salt concentration of at least 0.01 M to no more than 1 M Na ion concentration (or other salts) at a pH 7.0 to 8.3 and a temperature of at least 25° C. For example, conditions of 5×SSPE (750 mM NaCl, 50 mM NaPhosphate, 5 mM EDTA, pH 7.4) and a temperature of 25-30° C. are suitable for allele-specific probe hybridizations. For stringent conditions, see for example, Sambrook, Fritsche and Maniatis. "Molecular Cloning A laboratory Manual" $2^{nd}$ Ed. Cold Spring Harbor Press (1989) and Anderson "Nucleic Acid Hybridization" $1^{st}$ Ed., BIOS Scientific Publishers Limited (1999), which are hereby incorporated by reference in its entirety for all purposes above. "Hybridizing specifically to" or "specifically hybridizing to" or like expressions refer to the binding, duplexing, or hybridizing of a molecule substantially to or only to a particular nucleotide sequence or sequences under stringent conditions when that sequence is present in a complex mixture (e.g., total cellular) DNA or RNA.

"Inducible" or "inducible control" in reference to gene expression means that gene expression is controlled by a promoter and possibly of regulatory elements such that a promoter is transcriptionally active under a specific set of conditions, e.g., a change in physical conditions, such as a change in pH, temperature, salt concentration, or the like, or the presence of a particular chemical signal or combination of chemical signals that, for example, affect binding of the transcriptional activator to the promoter and/or affect function of the transcriptional activator itself.

"Ligation" means to form a covalent bond or linkage between the termini of two or more nucleic acids, e.g. oligonucleotides and/or polynucleotides, in a template-driven reaction. The nature of the bond or linkage may vary widely and the ligation may be carried out enzymatically or chemically. As used herein, ligations are usually carried out enzymatically to form a phosphodiester linkage between a 5' carbon of a terminal nucleotide of one oligonucleotide with 3' carbon of another oligonucleotide. A variety of template-driven ligation reactions are described in the following references, which are incorporated by reference: Whitely et al, U.S. Pat. No. 4,883,750; Letsinger et al, U.S. Pat. No. 5,476,930; Fung et al, U.S. Pat. No. 5,593,826; Kool, U.S. Pat. No. 5,426,180; Landegren et al, U.S. Pat. No. 5,871,921; Xu and Kool, Nucleic Acids Research, 27: 875-881 (1999); Higgins et al, Methods in Enzymology, 68: 50-71 (1979); Engler et al, The Enzymes, 15: 3-29 (1982); and Namsaraev, U.S. patent publication 2004/0110213.

"Nucleic acid construct" is used synonymously with "recombinant DNA molecule."

"Nucleoside" as used herein includes the natural nucleosides, including 2'-deoxy and 2'-hydroxyl forms, e.g. as described in Kornberg and Baker, DNA Replication, 2nd Ed. (Freeman, San Francisco, 1992). "Analogs" in reference to nucleosides includes synthetic nucleosides having modified base moieties and/or modified sugar moieties, e.g. described by Scheit, Nucleotide Analogs (John Wiley, New York, 1980); Uhlman and Peyman, Chemical Reviews, 90: 543-584 (1990), or the like, with the proviso that they are capable of specific hybridization. Such analogs include synthetic nucleosides designed to enhance binding properties, reduce complexity, increase specificity, and the like. Polynucleotides comprising analogs with enhanced hybridization or nuclease resistance properties are described in Uhlman and Peyman (cited above); Crooke et al, Exp. Opin. Ther. Patents, 6: 855-

870 (1996); Mesmaeker et al, Current Opinion in Structual Biology, 5: 343-355 (1995); and the like. Exemplary types of polynucleotides that are capable of enhancing duplex stability include oligonucleotide N3'→P5' phosphoramidates (referred to herein as "amidates"), peptide nucleic acids (referred to herein as "PNAs"), oligo-2'-O-alkylribonucleotides, polynucleotides containing C-5 propynylpyrimidines, locked nucleic acids (LNAs), and like compounds. Such oligonucleotides are either available commercially or may be synthesized using methods described in the literature.

"Polymerase chain reaction," or "PCR," means a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g. exemplified by the references: McPherson et al, editors, PCR: A Practical Approach and PCR2: A Practical Approach (IRL Press, Oxford, 1991 and 1995, respectively). For example, in a conventional PCR using Taq DNA polymerase, a double stranded target nucleic acid may be denatured at a temperature >90° C., primers annealed at a temperature in the range 50-75° C., and primers extended at a temperature in the range 72-78° C. Reaction volumes typically range from a few hundred nanoliters, e.g. 200 nL, to a few hundred µL, e.g. 200 µL.

"Polynucleotide" or "oligonucleotide" are used interchangeably and each mean a linear polymer of nucleotide monomers. Monomers making up polynucleotides and oligonucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, or the like. Such monomers and their internucleosidic linkages may be naturally occurring or may be analogs thereof, e.g. naturally occurring or non-naturally occurring analogs. Non-naturally occurring analogs may include PNAs, phosphorothioate internucleosidic linkages, bases containing linking groups permitting the attachment of labels, such as fluorophores, or haptens, and the like. Whenever the use of an oligonucleotide or polynucleotide requires enzymatic processing, such as extension by a polymerase, ligation by a ligase, or the like, one of ordinary skill would understand that oligonucleotides or polynucleotides in those instances would not contain certain analogs of internucleosidic linkages, sugar moieties, or bases at any or some positions. Polynucleotides typically range in size from a few monomeric units, e.g. 5-40, when they are usually referred to as "oligonucleotides," to several thousand monomeric units. Whenever a polynucleotide or oligonucleotide is represented by a sequence of letters (upper or lower case), such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, "I" denotes deoxyinosine, "U" denotes uridine, unless otherwise indicated or obvious from context. Unless otherwise noted the terminology and atom numbering conventions will follow those disclosed in Strachan and Read, Human Molecular Genetics 2 (Wiley-Liss, New York, 1999). Usually polynucleotides comprise the four natural nucleosides (e.g. deoxyadenosine, deoxycytidine, deoxyguanosine, deoxythymidine for DNA or their ribose counterparts for RNA) linked by phosphodiester linkages; however, they may also comprise non-natural nucleotide analogs, e.g. including modified bases, sugars, or internucleosidic linkages. It is clear to those skilled in the art that where an enzyme has specific oligonucleotide or polynucleotide substrate requirements for activity, e.g. single stranded DNA, RNA/DNA duplex, or the like, then selection of appropriate composition for the oligonucleotide or polynucleotide substrates is well within the knowledge of one of ordinary skill, especially with guidance from treatises, such as Sambrook et al, Molecular Cloning, Second Edition (Cold Spring Harbor Laboratory, New York, 1989), and like references.

"Primer" means an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process are determined by the sequence of the template polynucleotide. Usually primers are extended by a DNA polymerase. Primers usually have a length in the range of from 14 to 36 nucleotides.

"Recombination element" means a sequence that is a site of recombination of DNA sequences in a recombination reaction. A recombination element may be a segment of DNA that is homologous to another segment that participates in a recombination reaction (e.g. as in homologous recombination), or it may be a specific sequence where recombination takes place by action of an associated recombinase, and perhaps additional ancillary factors, that recognizes all or part of the specific sequence (e.g. as in site-specific recombination). In one aspect, a recombination element is a recombination site of a site-specific recombination system, such as Cre-LoxP, Flp-FRT, or the like.

"Regulatory elements" in reference to gene expression means DNA sequences that are operably linked to the expression of one or more genes. Such elements are commonly located at positions adjacent to the expressed genes and can include promoters, terminators, antiterminators, activators, attenuators, and the like, e.g. Kornberg and Baker, DNA Replication, $2^{nd}$ Edition (Freeman, San Francisco, 1992), Makrides, Microbiological Reviews, 60: 512-538 (1996). Frequently, one or more co-regulated genes are associated with the same set of regulatory elements in an operon.

TABLE II

Novel Mutant LoxP Spacer Regions

| Spacer | Self Re-comb | Non-Self Re-comb | Total | Spacer | Self Re-comb | Non-Self Re-comb | Total |
|---|---|---|---|---|---|---|---|
| GGGTAGGC | 6 | 38 | 44 | TTGTAAGG | 0 | 1 | 1 |
| GGGTAGGT | 5 | 26 | 31 | GGTTACAT | 0 | 1 | 1 |
| GGGTAGGG | 4 | 38 | 42 | GGCTATGT | 0 | 2 | 2 |
| GAGTACGC | 2 | 4 | 6 | GCCTAGCG | 0 | 1 | 1 |
| GTGTAGGG | 2 | 17 | 19 | GTGTAGCT | 0 | 4 | 4 |
| GGGTAAGC | 2 | 9 | 11 | GAGTACGT | 0 | 1 | 1 |

TABLE II-continued

Novel Mutant LoxP Spacer Regions

| Spacer | Self Re-comb | Non-Self Re-comb | Total | Spacer | Self Re-comb | Non-Self Re-comb | Total |
|---|---|---|---|---|---|---|---|
| TGGTATGT | 1 | 5 | 6 | GGCTAGGC | 0 | 3 | 3 |
| GCATAGGC | 1 | 2 | 3 | GCGTATGG | 0 | 2 | 2 |
| GGGTATTC | 1 | 4 | 5 | GCGTACGG | 0 | 1 | 1 |
| GGGTAGAT | 1 | 7 | 8 | AAATAGCC | 0 | 1 | 1 |
| GGGTAGTG | 1 | 10 | 11 | AGTTAGCC | 0 | 1 | 1 |
| TGGTATGC | 1 | 6 | 7 | TCGTAGCG | 0 | 2 | 2 |
| TGGTAGGG | 1 | 16 | 17 | GCGTAGCT | 0 | 1 | 1 |
| TTGTATGG | 1 | 3 | 4 | TAGTAGGT | 0 | 1 | 1 |
| CGGTAGGG | 1 | 6 | 7 | GAGTAGGT | 0 | 5 | 5 |
| GGTTAGGC | 1 | 5 | 6 | GTGTAAAT | 0 | 1 | 1 |
| TGGTAGTT | 1 | 6 | 7 | GCCTAAAT | 0 | 1 | 1 |
| GGGTAGAC | 1 | 5 | 6 | GGGTATCG | 0 | 2 | 2 |
| GTGTAGGA | 1 | 6 | 7 | GTTTACGG | 0 | 1 | 1 |
| GTGTAGGC | 1 | 15 | 16 | TGGTAATT | 0 | 1 | 1 |
| GTGTAGTC | 1 | 3 | 4 | GCGTAAGT | 0 | 2 | 2 |
| TCGTAGGC | 1 | 1 | 2 | ACGTAAGG | 0 | 1 | 1 |
| GGGTAGTT | 1 | 11 | 12 | GGATATGG | 0 | 1 | 1 |
| GGGTAGCG | 1 | 4 | 5 | GTCTAGAC | 0 | 1 | 1 |
| GGTTACGG | 1 | 1 | 2 | GATTACGG | 0 | 1 | 1 |
| GGATAGTA | 1 | 1 | 2 | TATTACGC | 0 | 1 | 1 |
| GTGTATTT | 1 | 2 | 3 | TCGTATGT | 0 | 1 | 1 |
| GCGTATGT | 1 | 1 | 2 | CCGTATGT | 0 | 1 | 1 |
| GGCTATAG | 1 | 0 | 1 | GGTTACGC | 0 | 1 | 1 |
| GTATAGTA | 1 | 1 | 2 | GTTTACGC | 0 | 2 | 2 |
| TTTTAGGT | 1 | 0 | 1 | TGCTAGGG | 0 | 2 | 2 |
| TGGTAGGC | 0 | 23 | 23 | GGATAGCA | 0 | 1 | 1 |
| TGGTAGGT | 0 | 14 | 14 | TGATAGCC | 0 | 1 | 1 |
| GGGTATGG | 0 | 18 | 18 | TGGTAACG | 0 | 1 | 1 |
| GTGTATGG | 0 | 6 | 6 | TTGTAGTG | 0 | 2 | 2 |
| AGGTAGGC | 0 | 5 | 5 | AAGTAGGT | 0 | 1 | 1 |
| TGGTAGTC | 0 | 9 | 9 | TGGTATTA | 0 | 1 | 1 |
| CGGTAGTT | 0 | 2 | 2 | GGTTAGTT | 0 | 3 | 3 |
| TTGTATGT | 0 | 2 | 2 | GTTTAGGA | 0 | 2 | 2 |
| GTGTATGT | 0 | 5 | 5 | GCATAAGC | 0 | 1 | 1 |
| TTGTATTC | 0 | 1 | 1 | GAATAGGC | 0 | 2 | 2 |
| GTGTATTA | 0 | 1 | 1 | GGTTAGGT | 0 | 1 | 1 |
| GCGTATGC | 0 | 3 | 3 | GATTAGGT | 0 | 2 | 2 |
| GATTAGGC | 0 | 4 | 4 | TAGTATGC | 0 | 1 | 1 |
| GCGTAGGT | 0 | 7 | 7 | TGCTAGGC | 0 | 1 | 1 |
| GGGTAAAT | 0 | 2 | 2 | GGCTAGGG | 0 | 4 | 4 |
| GCATAGGG | 0 | 1 | 1 | TGTTATAC | 0 | 1 | 1 |
| GCGTATAT | 0 | 2 | 2 | GTTTAAGC | 0 | 2 | 2 |
| GCTTATGT | 0 | 1 | 1 | AAGTAGGC | 0 | 2 | 2 |
| TGGTATCA | 0 | 1 | 1 | CGGTAAGC | 0 | 1 | 1 |
| GGGTATCC | 0 | 1 | 1 | GAGTAAAT | 0 | 1 | 1 |
| TGTTAGGC | 0 | 3 | 3 | GGTTACGT | 0 | 1 | 1 |
| AGTTAGGT | 0 | 1 | 1 | TGTTACGT | 0 | 1 | 1 |
| CGGTAGGA | 0 | 1 | 1 | CGTTACGC | 0 | 1 | 1 |
| GGGTATGC | 0 | 15 | 15 | GCATAGAT | 0 | 1 | 1 |
| GGATAGGC | 0 | 6 | 6 | GCATAGAC | 0 | 1 | 1 |
| GGGTACGC | 0 | 14 | 14 | TGTTAGTG | 0 | 2 | 2 |
| GTGTATCG | 0 | 1 | 1 | TTGTAGGG | 0 | 2 | 2 |
| GTGTAATG | 0 | 6 | 6 | TTGTATTT | 0 | 1 | 1 |
| TGGTAAGC | 0 | 3 | 3 | GGGTAAGG | 0 | 1 | 1 |
| GGGTAAGA | 0 | 3 | 3 | TGATATGG | 0 | 1 | 1 |
| TGGTAGAC | 0 | 2 | 2 | AGATATGT | 0 | 1 | 1 |
| TGGTACGT | 0 | 3 | 3 | TCGTAGTG | 0 | 1 | 1 |
| GGGTACGT | 0 | 6 | 6 | GTATACGC | 0 | 1 | 1 |
| TGGTAGGA | 0 | 10 | 10 | TTGTAAGT | 0 | 1 | 1 |
| GGATAGCC | 0 | 1 | 1 | CTGTAAGC | 0 | 1 | 1 |
| GTGTAGAC | 0 | 5 | 5 | TCATAGTC | 0 | 1 | 1 |
| GAGTACTG | 0 | 1 | 1 | GCATAGTA | 0 | 2 | 2 |
| TGGTAGTA | 0 | 2 | 2 | ACGTAGGG | 0 | 1 | 1 |
| TGGTAGAA | 0 | 1 | 1 | GCATACTA | 0 | 1 | 1 |
| ATGTAGGG | 0 | 3 | 3 | GGATAAGT | 0 | 2 | 2 |
| CTGTAGGC | 0 | 2 | 2 | GGCTAGAT | 0 | 1 | 1 |
| GTGTAGTT | 0 | 4 | 4 | GCGTAGTG | 0 | 3 | 3 |
| GTTTACTT | 0 | 1 | 1 | TACTAGAC | 0 | 1 | 1 |
| TGGTATGG | 0 | 5 | 5 | GACTAGAC | 0 | 1 | 1 |
| GAGTATGA | 0 | 3 | 3 | GGTTAAGT | 0 | 1 | 1 |
| GGGTATTA | 0 | 2 | 2 | GGATAACT | 0 | 1 | 1 |
| AGGTAGGT | 0 | 1 | 1 | TGGTAGCC | 0 | 1 | 1 |

TABLE II-continued

Novel Mutant LoxP Spacer Regions

| Spacer | Self Re-comb | Non-Self Re-comb | Total | Spacer | Self Re-comb | Non-Self Re-comb | Total |
|---|---|---|---|---|---|---|---|
| GCGTAATG | 0 | 2 | 2 | TTGTAGCA | 0 | 1 | 1 |
| GCGTACAG | 0 | 1 | 1 | TGGTAGCA | 0 | 1 | 1 |
| GTGTACGT | 0 | 1 | 1 | TGTTATGC | 0 | 1 | 1 |
| GTGTAGGT | 0 | 4 | 4 | GGTTATGG | 0 | 1 | 1 |
| TCGTAGGT | 0 | 2 | 2 | TCATAGAA | 0 | 1 | 1 |
| CCGTAGGT | 0 | 2 | 2 | TGATACGA | 0 | 1 | 1 |
| GTATAGTG | 0 | 1 | 1 | GTTTACAT | 0 | 1 | 1 |
| TCGTAGGA | 0 | 2 | 2 | GTTTAGAT | 0 | 1 | 1 |
| GCGTAGGA | 0 | 7 | 7 | GGGTACCC | 0 | 3 | 3 |
| GCGTAGAC | 0 | 2 | 2 | GTTTAGCT | 0 | 1 | 1 |
| AGTTAGGA | 0 | 1 | 1 | GTGTATGA | 0 | 2 | 2 |
| TGGTAGCG | 0 | 2 | 2 | CTGTATGG | 0 | 1 | 1 |
| TACTATGG | 0 | 1 | 1 | GGCTAGGA | 0 | 3 | 3 |
| GGGTAACT | 0 | 2 | 2 | GAGTATAC | 0 | 1 | 1 |
| TTGTAGGT | 0 | 1 | 1 | GAGTATAG | 0 | 1 | 1 |
| TGCTAGTG | 0 | 2 | 2 | TACTACTC | 0 | 1 | 1 |
| GGCTAGTG | 0 | 2 | 2 | GACTACTA | 0 | 1 | 1 |
| GGGTAAGT | 0 | 5 | 5 | TCATAGGC | 0 | 1 | 1 |
| TCGTATTG | 0 | 1 | 1 | GTATAGTT | 0 | 1 | 1 |
| TCGTAGGG | 0 | 4 | 4 | AGCTAGGG | 0 | 1 | 1 |
| GTTTATGT | 0 | 1 | 1 | CGGTATGC | 0 | 2 | 2 |
| GGGTAGTA | 0 | 5 | 5 | GACTAGCG | 0 | 1 | 1 |
| GGGTATGT | 0 | 10 | 10 | GCGTAAGG | 0 | 1 | 1 |
| GACTAAAT | 0 | 1 | 1 | GCGTACGC | 0 | 1 | 1 |
| GGGTACTC | 0 | 2 | 2 | ACGTACGT | 0 | 1 | 1 |
| GCGTAGGC | 0 | 5 | 5 | GGCTATTC | 0 | 1 | 1 |
| GAGTAGGG | 0 | 7 | 7 | GCATACGA | 0 | 1 | 1 |
| GTGTAGCC | 0 | 1 | 1 | GGATAGGA | 0 | 2 | 2 |
| CTGTAGCC | 0 | 1 | 1 | GGGTAACA | 0 | 1 | 1 |
| AGGTAGGG | 0 | 5 | 5 | AGCTAGGC | 0 | 1 | 1 |
| CGGTAGGC | 0 | 5 | 5 | GGATAATT | 0 | 1 | 1 |
| GCGTAGTC | 0 | 3 | 3 | GGGTACTA | 0 | 1 | 1 |
| GTGTACAT | 0 | 1 | 1 | TTTTATGG | 0 | 2 | 2 |
| GGTTATAT | 0 | 1 | 1 | TTATATTG | 0 | 1 | 1 |
| GGCTAGGT | 0 | 4 | 4 | TTGTACGC | 0 | 3 | 3 |
| GCTTAGTC | 0 | 1 | 1 | GTGTACGA | 0 | 1 | 1 |
| GGGTAGGA | 0 | 26 | 26 | GCGTAGAG | 0 | 2 | 2 |
| GAGTATGC | 0 | 5 | 5 | TGATAGGT | 0 | 1 | 1 |
| TGGTAATC | 0 | 2 | 2 | TTATAGGG | 0 | 1 | 1 |
| GGGTAATG | 0 | 3 | 3 | GGGTAAAC | 0 | 1 | 1 |
| TGCTAGTT | 0 | 1 | 1 | GCGTAGTT | 0 | 1 | 1 |
| GGCTAGTT | 0 | 3 | 3 | GTTTAGCC | 0 | 1 | 1 |
| GGGTAGAG | 0 | 6 | 6 | GAGTAGTC | 0 | 2 | 2 |
| GCATATGC | 0 | 2 | 2 | GTTTATGC | 0 | 3 | 3 |
| GGCTACGC | 0 | 2 | 2 | TAGTAGGG | 0 | 1 | 1 |
| AGATAGGG | 0 | 1 | 1 | CAGTAGGC | 0 | 1 | 1 |
| ATGTAGGA | 0 | 2 | 2 | GTATAGCG | 0 | 1 | 1 |
| GGATACGC | 0 | 1 | 1 | GCTTAGCC | 0 | 2 | 2 |
| GTGTAAGC | 0 | 4 | 4 | GTTTATGA | 0 | 1 | 1 |
| AGTTAGGG | 0 | 1 | 1 | GTTTAGTT | 0 | 1 | 1 |
| AGGTAAGG | 0 | 1 | 1 | GTTTAGTG | 0 | 1 | 1 |
| GAGTAGCG | 0 | 1 | 1 | GTCTAAAT | 0 | 1 | 1 |
| CAGTAGCC | 0 | 1 | 1 | GCTTAGGT | 0 | 1 | 1 |
| GGTTAGCT | 0 | 1 | 1 | GCGTATGA | 0 | 2 | 2 |
| GGCTATGG | 0 | 2 | 2 | GAATATGA | 0 | 1 | 1 |
| AGCTATGC | 0 | 1 | 1 | CGCTAGGC | 0 | 1 | 1 |
| GAATAGCC | 0 | 1 | 1 | GGGTAGCA | 0 | 1 | 1 |
| GAATAGCG | 0 | 1 | 1 | GACTAGCC | 0 | 1 | 1 |
| GGCTAACG | 0 | 1 | 1 | GGTTAGTC | 0 | 3 | 3 |
| GGGTATTG | 0 | 4 | 4 | TCGTATGA | 0 | 1 | 1 |
| TGGTAGTG | 0 | 6 | 6 | TGTTAGAT | 0 | 1 | 1 |
| GGATAGCT | 0 | 1 | 1 | AGTTAGAG | 0 | 1 | 1 |
| TTGTAGGC | 0 | 12 | 12 | TCTTATGC | 0 | 2 | 2 |
| GGGTAGAA | 0 | 2 | 2 | GCTTATGG | 0 | 1 | 1 |
| AGGTACGG | 0 | 1 | 1 | TGGTACGA | 0 | 2 | 2 |
| GGGTAATT | 0 | 2 | 2 | TGCTAGGA | 0 | 1 | 1 |
| GGGTAATC | 0 | 2 | 2 | CGCTAGGT | 0 | 1 | 1 |
| GACTAAGC | 0 | 1 | 1 | GTGTACAC | 0 | 1 | 1 |
| GAGTAAGC | 0 | 1 | 1 | TTGTAGCC | 0 | 1 | 1 |
| GCGTAGGG | 0 | 5 | 5 | GCATAGGT | 0 | 1 | 1 |
| TGATACGC | 0 | 1 | 1 | GCGTATTT | 0 | 1 | 1 |
| CGATACGG | 0 | 1 | 1 | TGATATAC | 0 | 1 | 1 |

TABLE II-continued

Novel Mutant LoxP Spacer Regions

| Spacer | Self Re-comb | Non-Self Re-comb | Total | Spacer | Self Re-comb | Non-Self Re-comb | Total |
|---|---|---|---|---|---|---|---|
| GTGTAGTG | 0 | 7 | 7 | GCGTAGCA | 0 | 1 | 1 |
| TGGTAAAC | 0 | 1 | 1 | GAGTAGAG | 0 | 1 | 1 |
| AGATATGG | 0 | 1 | 1 | TTGTAAGC | 0 | 1 | 1 |
| GGATATGC | 0 | 2 | 2 | GCTTAGAT | 0 | 1 | 1 |
| TTGTAGTC | 0 | 2 | 2 | GCTTAGAG | 0 | 1 | 1 |
| CTGTAGTC | 0 | 1 | 1 | AGATATGC | 0 | 1 | 1 |
| GGCTATGC | 0 | 2 | 2 | GGATATGA | 0 | 1 | 1 |
| TTCTATGC | 0 | 1 | 1 | GGCTAGAC | 0 | 1 | 1 |
| GTCTATGT | 0 | 1 | 1 | GGCTAGTC | 0 | 1 | 1 |
| GAGTAGGC | 0 | 5 | 5 | TAGTATGA | 0 | 1 | 1 |
| TGGTACGC | 0 | 6 | 6 | TGTTATGG | 0 | 1 | 1 |
| GTCTAGCG | 0 | 2 | 2 | TTGTATAC | 0 | 1 | 1 |
| GTGTAGCG | 0 | 3 | 3 | CAGTAGGA | 0 | 1 | 1 |
| TGGTACGG | 0 | 4 | 4 | GCGTACAT | 0 | 1 | 1 |
| GTGTAAGG | 0 | 6 | 6 | GGTTATTT | 0 | 1 | 1 |
| GAATAGGT | 0 | 1 | 1 | TGCTATGG | 0 | 1 | 1 |
| GGATATAT | 0 | 1 | 1 | GGATAGGT | 0 | 1 | 1 |
| GTGTATTG | 0 | 2 | 2 | GGGTAATA | 0 | 1 | 1 |
| GTTTAAAG | 0 | 1 | 1 | TGATAGGC | 0 | 1 | 1 |
| TTGTAGAC | 0 | 2 | 2 | GTATAGGT | 0 | 1 | 1 |
| GTGTAGAA | 0 | 2 | 2 | GAGTACGG | 0 | 1 | 1 |
| GGATAGAC | 0 | 2 | 2 | CAGTACGT | 0 | 1 | 1 |
| GGGTACGA | 0 | 2 | 2 | TTGTAGTA | 0 | 1 | 1 |
| ATTTACGA | 0 | 1 | 1 | GTGTAGTA | 0 | 1 | 1 |
| AGTTATGA | 0 | 1 | 1 | GGCTATAC | 0 | 1 | 1 |
| GGATATTG | 0 | 1 | 1 | TCATAGGG | 0 | 1 | 1 |
| TGCTACGT | 0 | 1 | 1 | GATTAGGA | 0 | 1 | 1 |
| GGTTAATG | 0 | 3 | 3 | TTATACGA | 0 | 1 | 1 |
| TTTTAAGA | 0 | 1 | 1 | TGTTAGGA | 0 | 1 | 1 |
| TTGTAGGA | 0 | 5 | 5 | AGGTAGAC | 0 | 1 | 1 |
| GGGTATAT | 0 | 2 | 2 | GCCTAGGG | 0 | 1 | 1 |
| GGGTATAC | 0 | 6 | 6 | CCCTAGGA | 0 | 1 | 1 |
| GTTTAGGG | 0 | 4 | 4 | CGTTAGCA | 0 | 1 | 1 |
| GCTTAGGG | 0 | 3 | 3 | ACGTAGGC | 0 | 1 | 1 |
| GCATAACG | 0 | 1 | 1 | ATGTAGAC | 0 | 1 | 1 |
| GTGTACGG | 0 | 3 | 3 | TTTTACAC | 0 | 1 | 1 |
| GTGTACGC | 0 | 3 | 3 | TGCTACAG | 0 | 1 | 1 |
| GGGTAGCC | 0 | 4 | 4 | TGATAAAG | 0 | 1 | 1 |
| GGGTAGCT | 0 | 1 | 1 | GACTATGC | 0 | 1 | 1 |
| GTTTAGGC | 0 | 3 | 3 | TATTACTG | 0 | 1 | 1 |
| AGGTACGC | 0 | 2 | 2 | TTATAGCG | 0 | 1 | 1 |
| GCATAGAG | 0 | 1 | 1 | GTATAGCC | 0 | 1 | 1 |
| CAGTAACC | 0 | 1 | 1 | GGTTATGC | 0 | 1 | 1 |
| CTGCATCC | 0 | 1 | 1 | GCATAGCG | 0 | 1 | 1 |
| GGATAGGG | 0 | 3 | 3 | AGGTACGT | 0 | 1 | 1 |
| GTCTATAG | 0 | 1 | 1 | TGTTAGCA | 0 | 1 | 1 |
| AAGTACTT | 0 | 1 | 1 | AGTTAGCG | 0 | 1 | 1 |
| AAGTAATT | 0 | 1 | 1 | TGGTAATG | 0 | 1 | 1 |
| TGGTAGAT | 0 | 2 | 2 | GCTTATGC | 0 | 1 | 1 |
| TTGTAGTT | 0 | 1 | 1 | GCGTAAAA | 0 | 1 | 1 |
| GGGTACGG | 0 | 4 | 4 | TCGTAGAG | 0 | 1 | 1 |
| GTGTACTC | 0 | 2 | 2 | GGCTAATG | 0 | 1 | 1 |
| GTGTATAT | 0 | 2 | 2 | TGATAGTC | 0 | 1 | 1 |
| GGGTACAT | 0 | 2 | 2 | CGATAGTC | 0 | 1 | 1 |
| GAGTAGTT | 0 | 1 | 1 | GTATAGGC | 0 | 1 | 1 |
| GCGTAGCG | 0 | 1 | 1 | TGTTAAGC | 0 | 1 | 1 |
| GGTTAGTG | 0 | 1 | 1 | TTATAGGC | 0 | 1 | 1 |
| TGGTACAC | 0 | 1 | 1 | GAGTAGTG | 0 | 2 | 2 |
| CACTATGC | 0 | 1 | 1 | GCTTAAGA | 0 | 1 | 1 |
| AACTATGG | 0 | 1 | 1 | CGGTAGGT | 0 | 1 | 1 |
| GGTTAGAG | 0 | 1 | 1 | CTGTAGGG | 0 | 2 | 2 |
| CCGTAGGG | 0 | 1 | 1 | ATGTACGG | 0 | 1 | 1 |
| GTCTAGGG | 0 | 2 | 2 | TTTTATGC | 0 | 1 | 1 |
| GAGTAGGA | 0 | 5 | 5 | TAGTAGTA | 0 | 1 | 1 |
| GGGTAGTC | 0 | 6 | 6 | GTTTACGA | 0 | 1 | 1 |
| TGGTAACC | 0 | 1 | 1 | GCCTACGC | 0 | 1 | 1 |
| GTGTACTT | 0 | 1 | 1 | GCTTAGCG | 0 | 1 | 1 |
| GTGTATAC | 0 | 2 | 2 | TCTTAGCA | 0 | 1 | 1 |
| GTTTATGG | 0 | 1 | 1 | CAGTATGC | 0 | 1 | 1 |
| GCTTACGA | 0 | 1 | 1 | GTATAGGA | 0 | 1 | 1 |
| GCTTAGTA | 0 | 1 | 1 | GACTAGGA | 0 | 1 | 1 |
| GGTTAAGC | 0 | 2 | 2 | GGGTAACG | 0 | 2 | 2 |

TABLE II-continued

Novel Mutant LoxP Spacer Regions

| Spacer | Self Re-comb | Non-Self Re-comb | Total | Spacer | Self Re-comb | Non-Self Re-comb | Total |
|---|---|---|---|---|---|---|---|
| AGTTAGGC | 0 | 1 | 1 | GGGTACTG | 0 | 2 | 2 |
| TAGTAGGA | 0 | 1 | 1 | AGGTACAC | 0 | 1 | 1 |
| AAGTAGGG | 0 | 2 | 2 | GGGTACAG | 0 | 2 | 2 |
| TGGTAGAG | 0 | 3 | 3 | GGATACTG | 0 | 1 | 1 |
| TAGTACGG | 0 | 1 | 1 | CATTAGGT | 0 | 1 | 1 |
| GCGTATCT | 0 | 1 | 1 | GTGTAAGA | 0 | 3 | 3 |
| TAGTATGT | 0 | 1 | 1 | GGGTATGA | 0 | 6 | 6 |
| GAGTATGG | 0 | 3 | 3 | CGGTATGT | 0 | 1 | 1 |
| TGGTATGA | 0 | 1 | 1 | GGTTAGGG | 0 | 2 | 2 |
| GGCTAAAG | 0 | 1 | 1 | GTCTAGGT | 0 | 1 | 1 |
| GAATATGG | 0 | 1 | 1 | TTTTAGGA | 0 | 1 | 1 |
| GGGTATTT | 0 | 5 | 5 | TAGTAGGC | 0 | 2 | 2 |
| GTGTAAGT | 0 | 3 | 3 | | | | |

TABLE III

Unique Mutant LoxP Spacer Pairs

| LE | RE | No. Occurrences | LE | RE | No. Occurrences |
|---|---|---|---|---|---|
| TGGTAGGC | GGGTAGGG | 6 | GCGTAAGT | ACGTAAGG | 1 |
| GGGTAGGC | GGGTAGGC | 6 | GCTTAGGG | GGATATGG | 1 |
| TGGTAGGA | GGGTAGGG | 5 | GTCTAGAC | GTGTAGGC | 1 |
| GGGTAGGC | GGGTAGGA | 5 | GATTACGG | TATTACGC | 1 |
| GGGTAGGT | GGGTAGGG | 5 | TCGTATGT | CCGTATGT | 1 |
| GGGTAGGT | GGGTAGGT | 5 | GGTTACGC | GTTTACGC | 1 |
| TGGTAGGC | TGGTAGGT | 4 | GGCTAGGT | TGCTAGGG | 1 |
| GGGTAGGA | GGGTAGGG | 4 | GGATAGCA | TGATAGCC | 1 |
| GGGTAGGA | GGGTAGGT | 4 | TGGTAACG | TTGTAGTG | 1 |
| GGGTAGGG | GGGTAGGG | 4 | GAGTAGGT | AAGTAGGT | 1 |
| TGGTATGC | GGGTATGG | 3 | TGGTAGGG | CGGTAGGG | 1 |
| TGGTAGGG | GGGTAGGG | 3 | TTGTAGAC | GTGTAGAC | 1 |
| GGGTAGGC | GGGTAGGT | 3 | TGGTAGGG | TGCTAGGG | 1 |
| GGGTATGC | GGGTATGG | 3 | GGTTAGTT | GGGTAGAT | 1 |
| GTGTAGTT | GTGTAGTG | 3 | GTGTAGGA | GTTTAGGA | 1 |
| GGGTAGGC | AGGTAGGG | 3 | GCATAAGC | GAATAGGC | 1 |
| GGGTATGG | GTGTATGG | 2 | GGTTAGGT | GATTAGGT | 1 |
| GGGTAGGC | AGGTAGGC | 2 | TAGTATGC | TGGTAAGC | 1 |
| GTGTAATG | GGGTAGGG | 2 | TGCTAGGC | GGCTAGGG | 1 |
| TGGTAGGC | CGGTAGGG | 2 | TGGTACGC | TGTTATAC | 1 |
| AGGTAGGC | GGGTAGGG | 2 | GGGTAATC | GGGTAAGC | 1 |
| TGGTAGTT | GGGTAGTG | 2 | GGGTAGAC | GTTTAAGC | 1 |
| TGGTAGGG | CGGTAGGC | 2 | GGGTATCG | GTGTAAGG | 1 |
| GGGTAAGC | GGGTAAGC | 2 | TGGTATGC | TGGTAGGC | 1 |
| TGGTAGTC | TGGTAGTG | 2 | TGGTAGTA | GGGTAGTA | 1 |
| TTGTAGGC | GTGTAGGC | 2 | GTGTAGAC | GTGTAGAA | 1 |
| GGGTAAGC | GGGTAGGC | 2 | GAGTAGGG | AAGTAGGC | 1 |
| GGGTACGC | GGGTAGGC | 2 | GGGTAAGC | CGGTAAGC | 1 |
| GTGTACGG | GTGTACGC | 2 | GAGTAAAT | GGTTACGT | 1 |
| TGGTAGGA | GGGTAGGA | 2 | GGCTACGC | GGGTACGC | 1 |
| TGGTAGGG | GGGTAGGC | 2 | TGTTACGT | CGTTACGC | 1 |
| GTGTAGGA | GTGTAGGG | 2 | GCATAGAT | GCATAGAC | 1 |
| GGGTATAC | GTGTATAC | 2 | TGTTAGTG | TTGTAGGG | 1 |
| GGGTAAGT | GGGTATGT | 2 | GGGTAAGA | GGGTAAGG | 1 |
| TGGTAGGC | GGGTAGGT | 2 | GCGTAGGT | GTGTAGGT | 1 |
| GAGTACGC | GAGTACGC | 2 | TTGTATGG | TTGTATGG | 1 |
| GTGTAGGG | GTGTAGGG | 2 | GGGTATTA | GGGTATGA | 1 |
| TGGTAGTC | GGGTAGTC | 2 | GGGTATGA | GGGTATGG | 1 |
| GTGTAGGC | GTGTAGGG | 2 | GTGTAGGG | ATGTAGGA | 1 |
| GTGTAAGA | GTGTAAGG | 2 | GGGTATAC | GGGTAAGC | 1 |
| TGGTAGGT | GGGTAGGG | 2 | GAGTAGGT | GCGTAGGT | 1 |
| GGGTATGA | GGGTAGGA | 2 | TGATATGG | AGATATGT | 1 |
| GGGTATAC | GGCTAGGC | 2 | GGGTAGAA | TGGTAGAG | 1 |
| GGGTATTT | GGGTAGAT | 2 | TCGTAGTG | GCGTAGTC | 1 |
| GAGTAGGA | GAGTAGGG | 2 | GTATACGC | GGATATGC | 1 |
| GGGTAGTT | GGGTAGTG | 2 | TTGTAAGT | CTGTAAGC | 1 |
| GTGTAGGA | GTGTAGGC | 2 | TCATAGTC | GCATAGTA | 1 |
| TTGTAGGC | GTGTAGGG | 2 | GGGTAGGG | GTGTATGG | 1 |
| TTGTAGGC | CTGTAGGC | 2 | GGGTATGT | GATTAGGT | 1 |
| TGGTAGTC | CGGTAGTT | 1 | GGGTATTG | GGGTAGTG | 1 |
| TTGTATGT | GTGTATGT | 1 | GCGTAGGT | ACGTAGGG | 1 |
| TTGTATTC | GTGTATTA | 1 | GCATAGTA | GCATACTA | 1 |
| GCGTATGC | GATTAGGC | 1 | GGATAAGT | GGCTAGAT | 1 |
| TGGTAGGT | TGGTATGT | 1 | GAGTACGC | GAGTATGC | 1 |

TABLE III-continued

Unique Mutant LoxP Spacer Pairs

| LE | RE | No. Occurrences | LE | RE | No. Occurrences |
|---|---|---|---|---|---|
| GCGTAGGT | GGGTAAAT | 1 | GGGTAGGG | GCGTAGTG | 1 |
| GCATAGGC | GCATAGGG | 1 | GGGTAGGA | GTTTAGGA | 1 |
| GCGTATAT | GCTTATGT | 1 | TACTAGAC | GACTAGAC | 1 |
| TGGTATCA | GGGTATCC | 1 | GGTTAAGT | GGATAACT | 1 |
| TGTTAGGC | AGTTAGGT | 1 | TGGTAGGC | TGGTAGCC | 1 |
| TGGTAGGT | CGGTAGGA | 1 | TTGTAGCA | TGGTAGCA | 1 |
| GGGTATTC | GGGTATGC | 1 | GGGTAGCC | GTGTAGTC | 1 |
| GGATAGGC | GGGTACGC | 1 | GAGTAGGT | AAGTAGGC | 1 |
| GTGTATCG | GTGTAATG | 1 | GCATATGC | GGGTATGC | 1 |
| TGGTAAGC | GGGTAAGA | 1 | GGCTATAG | GGCTATAG | 1 |
| TGGTAGAC | GGGTAGAT | 1 | GTGTAGTC | GTGTAGGC | 1 |
| TGGTACGT | GGGTACGT | 1 | TGTTATGC | GGTTATGG | 1 |
| GGATAGCC | GTGTAGAC | 1 | TCATAGAA | TGATACGA | 1 |
| GAGTACTG | GGGTAGTG | 1 | TGGTACGC | TGGTACGG | 1 |
| TGGTAGTA | TGGTAGAA | 1 | GGGTATTC | GTTTAGGC | 1 |
| ATGTAGGG | CTGTAGGC | 1 | GTGTAGGG | GCTTAGGG | 1 |
| GTGTAGTT | GCGTAGGT | 1 | GTTTACAT | GTTTAGAT | 1 |
| GTTTACTT | GGGTAGGT | 1 | GGGTACCC | GGGTATTC | 1 |
| TTGTATGG | TGGTATGG | 1 | GGGTAGGC | GGGTAGGG | 1 |
| GAGTACGC | GGGTACGC | 1 | GGGTAGCC | GGGTACGC | 1 |
| GAGTATGA | GGGTATTA | 1 | GGGTAGTT | GTTTAGCT | 1 |
| GGGTAGGC | AGGTAGGT | 1 | GTGTATGA | CTGTATGG | 1 |
| GCGTAATG | GCGTACAG | 1 | GGTTAGGC | GGTTAGGC | 1 |
| GTGTACGT | GTGTAGGT | 1 | GGCTAGGA | GGGTAGGA | 1 |
| TCGTAGGT | CCGTAGGT | 1 | GGGTAGGC | CGGTAGGG | 1 |
| GTGTAATG | GTATAGTG | 1 | GAGTATAC | GAGTATAG | 1 |
| TCGTAGGA | GCGTAGGA | 1 | GGATAAGT | GGCTAGGT | 1 |
| GCGTAGAC | GTGTAGAC | 1 | TACTACTC | GACTACTA | 1 |
| GGTTAGGC | AGTTAGGA | 1 | TGGTAGAC | GGGTAGAC | 1 |
| TGGTAGTT | TGGTAGTT | 1 | TCATAGGC | GCATAGGC | 1 |
| TGGTAGCG | TACTATGG | 1 | GTATAGTA | GTATAGTT | 1 |
| GGGTAACT | GTGTATGT | 1 | AGCTAGGG | GGCTAGGA | 1 |
| TTGTAGGT | GTGTAGGG | 1 | GTATAGTA | GTATAGTA | 1 |
| TGCTAGTG | GGCTAGTG | 1 | GCGTAATG | GCGTAGTG | 1 |
| GGGTAAGT | GGGTAGGT | 1 | CGGTATGC | GGGTATGG | 1 |
| TCGTATTG | TCGTAGGG | 1 | GACTAGCG | GTGTATGG | 1 |
| GGGTAGAT | GTTTATGT | 1 | GCGTAAGG | GCGTAGGG | 1 |

TABLE III-continued

Unique Mutant LoxP Spacer Pairs

| LE | RE | No. Occurrences | LE | RE | No. Occurrences |
|---|---|---|---|---|---|
| TGGTAGTT | GGGTAGTA | 1 | GGGTAGTT | CGGTAGTT | 1 |
| GGGTATGT | GACTAAAT | 1 | TGGTAGGC | TGGTAGGG | 1 |
| GGGTACTC | GGGTAGGC | 1 | GCGTACGC | ACGTACGT | 1 |
| GCGTAGGC | GGATAGGC | 1 | GGCTATTC | GGGTACGC | 1 |
| GTGTAGGG | GAGTAGGG | 1 | GCATACGA | GGATAGGA | 1 |
| GTGTAGCC | CTGTAGCC | 1 | GGGTAGGA | GGGTAACA | 1 |
| TGGTAGGA | AGGTAGGG | 1 | GGCTAGGA | AGCTAGGC | 1 |
| GCGTAGTC | GGGTAGGC | 1 | GGGTAGTC | GGGTATTC | 1 |
| GTGTACAT | GGTTATAT | 1 | TCGTAGGA | GCGTAGGT | 1 |
| TGGTACGT | GGGTACGC | 1 | GGGTAAGT | GGATAATT | 1 |
| GGCTAGGT | GGGTAGGT | 1 | GGGTACTA | GGGTACTG | 1 |
| GCTTAGTC | GGGTACGC | 1 | TTTTATGG | TTATATTG | 1 |
| GAGTATGC | GGGTATGC | 1 | TGGTAGGT | GGGTAGGA | 1 |
| TGGTAATC | GGGTAATG | 1 | CGGTAGGG | CGGTAGGG | 1 |
| TGCTAGTT | GGCTAGTT | 1 | GAGTAGGC | GAGTAGGG | 1 |
| GGGTAGAC | GGGTAGAG | 1 | GGGTAGTT | GGGTAGTA | 1 |
| GCATATGC | GGCTACGC | 1 | TTGTACGC | GTGTACGA | 1 |
| GGATAGGC | AGATAGGG | 1 | GCGTAGAG | GGGTAGGG | 1 |
| GTGTAGGA | ATGTAGGA | 1 | TGATAGGT | TCGTAGGT | 1 |
| GGATACGC | GTGTAAGC | 1 | GATTAGGC | GAGTATGC | 1 |
| AGTTAGGG | AGGTAAGG | 1 | TGGTAGCG | TTATAGGG | 1 |
| GAGTAGCG | CAGTAGCC | 1 | GGGTAAAC | GGGTAGGC | 1 |
| GGGTATGT | GGTTAGCT | 1 | GCGTAGTT | GCGTAAGT | 1 |
| GGCTATGG | AGCTATGC | 1 | GTTTAGCC | GAGTAGTC | 1 |
| GAATAGCC | GAATAGCG | 1 | GGGTAGCC | GTTTATGC | 1 |
| GGCTAACG | GGGTATTG | 1 | GCGTAGAC | GTGTACTC | 1 |
| GGGTATGT | TGGTATGC | 1 | TAGTAGGC | TAGTAGGG | 1 |
| GGCTAGGT | GGATAGCT | 1 | GTGTAGGG | GGTTAATG | 1 |
| GGGTAGAC | GGGTAGAA | 1 | GAGTAGGA | CAGTAGGC | 1 |
| TGGTACGT | AGGTACGG | 1 | GGGTAGCG | GTATAGCG | 1 |
| GGGTAATT | GGGTAATC | 1 | GTGTATTT | GTGTAGCT | 1 |
| TGGTATGG | GGGTATGG | 1 | TGGTAGGG | TGGTAGGG | 1 |
| GGGTAGTG | GGGTATGG | 1 | GCATAGGC | GCATAGGC | 1 |
| GACTAAGC | GAGTAAGC | 1 | GGGTACCC | GCTTAGCC | 1 |
| GCGTAGGC | GCGTAGGG | 1 | TGGTAGAT | GGGTAGAG | 1 |
| TGATACGC | CGATACGG | 1 | TTTTATGG | GTTTATGA | 1 |

TABLE III-continued

Unique Mutant LoxP Spacer Pairs

| LE | RE | No. Occurrences | LE | RE | No. Occurrences |
|---|---|---|---|---|---|
| GTGTAGTC | GTGTAGTG | 1 | GAGTAGGC | GGGTATGC | 1 |
| TGGTAGGC | TGGTAAAC | 1 | GCGTATGC | GCGTATGG | 1 |
| AGATATGG | GGATATGC | 1 | TGGTAGGT | TGGTAGGG | 1 |
| TTGTAGTC | CTGTAGTC | 1 | CGGTAGGC | CGGTAGGG | 1 |
| TGGTAGGT | CGGTAGGG | 1 | GTTTAGTT | GTTTAGTG | 1 |
| TTCTATGC | GTCTATGT | 1 | TTGTAGGC | ATGTAGGG | 1 |
| GAGTACGC | GAGTAGGC | 1 | GGGTAGAG | GGGTAGCG | 1 |
| TGGTACGC | GGGTACGT | 1 | TGGTAGGC | AGGTAGGG | 1 |
| GTCTAGCG | GTGTAGCG | 1 | GTCTAAAT | GCTTAGGT | 1 |
| TCGTAGGC | TCGTAGGC | 1 | GCGTATGA | GAATATGA | 1 |
| TGGTAGGG | TGGTACGG | 1 | GGCTAGGG | CGCTAGGC | 1 |
| GTGTAAGC | GTGTAAGG | 1 | GGGTAGCA | GGGTAGGA | 1 |
| GGGTAGTT | GAATAGGT | 1 | GACTAGCC | GATTAGGC | 1 |
| GTGTAATG | GTGTAGCG | 1 | GCTTAGCC | GGTTAGTC | 1 |
| TGGTAGGG | GGGTAGGT | 1 | GCGTATGT | TCGTATGA | 1 |
| GGATATAT | GGGTATGT | 1 | GGCTATGG | GGCTATGT | 1 |
| GTGTATTG | GTTTAAAG | 1 | TGTTAGAT | AGTTAGAG | 1 |
| TTGTAGAC | GTGTAGAA | 1 | TCTTATGC | GCTTATGG | 1 |
| GGATAGAC | GTGTAGAC | 1 | TGGTACGA | TGGTACGC | 1 |
| GGGTACGA | GGGTACGC | 1 | TGCTAGGA | CGCTAGGT | 1 |
| ATTTACGA | AGTTATGA | 1 | GGGTAGTG | GGCTAGTG | 1 |
| GGATATTG | GGGTATGG | 1 | GGGTACGT | TGGTACGG | 1 |
| TGCTACGT | TGGTATGT | 1 | TTTTAGGT | TTTTAGGT | 1 |
| GGTTAATG | GGGTAGGG | 1 | GGGTAGTC | GGGTACCC | 1 |
| GGGTAGGG | GAGTAGGG | 1 | GGCTAGGG | GGGTAGGG | 1 |
| TTTTAAGA | TTGTAGGA | 1 | GTGTACAC | GGGTAGGC | 1 |
| GGGTATAT | GGGTAACT | 1 | GTTTAAGC | GTTTATGC | 1 |
| GGGTATAC | GGGTATGC | 1 | TTGTAGCC | GTGTAGCT | 1 |
| GAGTACGC | GGGTAGGC | 1 | GGGTAGAT | GGGTAGAT | 1 |
| GTGTAGCG | GTTTAGGG | 1 | GCGTATGA | GCGTAGGA | 1 |
| GCTTAGGG | GCATAACG | 1 | GGGTAGGC | GGTTAGTC | 1 |
| GGGTAGCC | GGGTAGCG | 1 | GGCTATGC | GGGTATGC | 1 |
| GGGTAGCG | GGGTAGCT | 1 | GCATAGGT | GCGTATTT | 1 |
| GTTTAGGC | GCGTAGGC | 1 | TGGTAGTC | TGGTAGTT | 1 |
| TGGTACGC | AGGTACGC | 1 | TGGTATGT | TGGTATGT | 1 |
| GCATAGAG | GTGTAGTG | 1 | GCGTAGGA | GCGTAGCA | 1 |
| GGTTACGG | GGTTACGG | 1 | TGGTAAGC | GGGTAAGC | 1 |
| TGGTAGGC | CGGTAGGC | 1 | GTGTAAGG | GAGTAGAG | 1 |
| CAGTAACC | CTGCATCC | 1 | TTGTAAGC | GTGTAAGA | 1 |
| GGATAGGG | GTCTATAG | 1 | GCTTAGAT | GCTTAGAG | 1 |
| GTGTAGGC | GTGTAGGC | 1 | GTGTAGGA | GTGTAGGA | 1 |
| AAGTACTT | AAGTAATT | 1 | TGGTAGGC | GGGTAGGC | 1 |
| TGGTAGAT | TTGTAGTT | 1 | TTGTAGGA | GTGTAGGC | 1 |
| GGATAGAC | GTGTAGGC | 1 | AGATATGC | GGATATGA | 1 |
| GTGTAGGC | GGGTACGC | 1 | GGCTAGAC | GGCTAGTC | 1 |
| GGGTACGT | GGGTACGG | 1 | TGGTAGTG | TGGTAGGG | 1 |
| GGGTATGT | TGGTATGT | 1 | TGGTAGTC | TTGTAGGC | 1 |
| GTGTACTC | GGATAGGC | 1 | GTGTAGGG | ATGTAGGG | 1 |
| GCGTATAT | GTGTATAT | 1 | GGGTACGT | GGGTAGGT | 1 |
| GGCTAGTT | GGGTACAT | 1 | GTCTAGGG | GTGTAAGG | 1 |
| GAGTAGTT | GGGTAGGT | 1 | TGTTAGGC | GGTTAGGC | 1 |
| GGGTAGTT | TGGTAGTG | 1 | GGGTAGGA | GGATAGTA | 1 |
| TGGTATGC | TGGTATGG | 1 | GAGTATGA | TAGTATGA | 1 |
| GTGTAGTC | GTGTAGTC | 1 | TGGTAGGT | GGGTAGGC | 1 |
| TTGTAGGA | GTGTAGGT | 1 | GCGTAGGG | GGGTAACG | 1 |
| GGTTAATG | GGGTAATG | 1 | TGTTATGG | TCGTAGGG | 1 |
| GCGTAGCG | GGTTAGTG | 1 | TGTTAGGC | GGTTAGGG | 1 |
| GTGTATAT | GGGTAGAT | 1 | TGGTAGGC | TTGTATAC | 1 |
| TGGTACAC | GGGTACAT | 1 | GGTTAGTC | GGTTAGGC | 1 |
| CACTATGC | AACTATGG | 1 | GAGTAGGA | CAGTAGGA | 1 |
| TCGTAGGG | CCGTAGGT | 1 | GTGTAGGG | TTGTAGGA | 1 |
| GGGTAGGC | GGGTAGAC | 1 | GCGTACAT | GGGTATGT | 1 |
| GGGTATTG | GGTTAGAG | 1 | GGTTATTT | GGTTAGTT | 1 |
| GCGTAGGG | CCGTAGGG | 1 | GTGTAAGT | GTGTAGGT | 1 |
| GGATAGTA | GGATAGTA | 1 | TGCTATGG | TGTTAGTG | 1 |
| GTGTAGGG | GTCTAGGG | 1 | GGATAGGT | GGATAGGA | 1 |
| GGATAGGG | GTTTAGGG | 1 | GGGTAATA | GGGTATGA | 1 |
| GCGTAGGA | GAGTAGGA | 1 | TGATAGGC | TTGTAGGC | 1 |
| GGGTAGTT | GGGTAGTC | 1 | GGGTACGT | GTATAGGT | 1 |
| GGGTATGC | TGGTATGG | 1 | GAGTACGG | CAGTACGT | 1 |
| TCGTAGGC | TGGTAACC | 1 | TTGTAGTA | GTGTAGTA | 1 |
| GGGTAGCG | GGGTAGCG | 1 | TGGTAGGT | CGGTAGGC | 1 |
| GTGTACTT | GTGTATTT | 1 | GTGTAGGC | GGGTAGGC | 1 |

TABLE III-continued

Unique Mutant LoxP Spacer Pairs

| LE | RE | No. Occurrences | LE | RE | No. Occurrences |
|---|---|---|---|---|---|
| GTTTATGG | GGGTAGGG | 1 | GGCTATAC | GGGTATGC | 1 |
| GCTTACGA | GGGTAGGA | 1 | GCGTAGGA | TCGTAGGG | 1 |
| GTGTATTG | GTTTAGGG | 1 | TCATAGGG | TTGTATGG | 1 |
| GCTTAGTA | GCGTAGGA | 1 | GATTAGGA | GGGTAGGA | 1 |
| GGTTAAGC | GGTTAGGC | 1 | TTATACGA | TGTTAGGA | 1 |
| AGTTAGGC | GGTTAGGC | 1 | AGGTAGAC | GGGTAGAG | 1 |
| TAGTAGGA | AAGTAGGG | 1 | GCGTAGTG | GCCTAGGG | 1 |
| TGGTAGAG | TAGTACGG | 1 | TGGTAGTC | GGGTAGTG | 1 |
| GGGTATGG | GTGTAGGG | 1 | GCGTAGGC | GGGTAGGC | 1 |
| TGGTACGC | TGGTAGGC | 1 | CCCTAGGA | CGTTAGCA | 1 |
| GGGTAGTT | GGGTAGAT | 1 | ACGTAGGC | GCGTAGGC | 1 |
| GGATAGGC | GGATAGGG | 1 | TTTTACAC | TTGTAGGC | 1 |
| TGGTATGC | TGGTATGC | 1 | TGCTACAG | TGATAAAG | 1 |
| GGGTATGT | GCGTATCT | 1 | GGGTAGGC | GAATAGGC | 1 |
| TAGTATGT | GAGTATGG | 1 | GCGTAGTC | GACTATGC | 1 |
| GGGTAGTT | TGGTAGTT | 1 | GTGTAGGG | TTGTAGGG | 1 |
| TGGTATGA | GGGTATGG | 1 | TGGTAGGT | GGGTAGGT | 1 |
| GGCTAAAG | GAATATGG | 1 | TATTACTG | TCGTAGCG | 1 |
| GGGTAGGT | GGGTATTT | 1 | TTATAGCG | GTATAGCC | 1 |
| GTGTAAGC | GGGTAAGC | 1 | GCGTATGC | GAGTATGC | 1 |
| GTGTAAGC | GTGTAAGT | 1 | GGGTACGC | GGGTACGG | 1 |
| CAGTATGC | GAGTATGA | 1 | GAGTAGGT | GGGTAGGT | 1 |
| GCGTATGT | GCGTATGT | 1 | GGTTATGC | GGGTAGGC | 1 |
| GTATAGGA | GACTAGGA | 1 | GTGTATGG | GCATAGCG | 1 |
| GGGTAACG | GGGTACTG | 1 | TGGTACGA | AGGTACGT | 1 |
| TGCTAGTG | GGCTAGTT | 1 | GGGTACAG | GAGTATGG | 1 |
| AGGTACAC | GGGTACAG | 1 | TGTTAGCA | AGTTAGCG | 1 |
| GGATACTG | GTGTAGGG | 1 | GGGTATAT | GGGTAAGT | 1 |
| GATTAGGC | CATTAGGT | 1 | TGGTAATC | TGGTAATG | 1 |
| GCGTAGGT | GTGTAAGT | 1 | AAGTAGGG | GAGTAGGG | 1 |
| GGGTACGC | GGGTAGTC | 1 | GAGTAGGC | GCTTATGC | 1 |
| CGGTATGT | TGGTATGG | 1 | GCGTAAAA | GCGTAGGA | 1 |
| GGGTAATT | GGGTAGGT | 1 | GGGTATGC | GGGTAAGC | 1 |
| GTGTAGGC | GTTTAGGC | 1 | TCGTAGAG | GCGTAGAG | 1 |
| TGGTAGTG | GGGTAGTA | 1 | GGGTACGG | TGGTACGG | 1 |
| GGTTACGG | GGTTAGGG | 1 | GGCTAATG | GGCTAGGG | 1 |
| GGGTAGGT | GTCTAGGT | 1 | GAGTAGGC | GTTTATGC | 1 |
| GTTTAGGG | TTTTAGGA | 1 | TGATAGTC | CGATAGTC | 1 |
| GGGTAGAG | GGGTAGGG | 1 | GGTTAGTT | GGGTAAAT | 1 |
| TTGTAGGC | TAGTAGGC | 1 | GGCTAGGC | GTATAGGC | 1 |
| TGGTAGAG | TTGTAAGG | 1 | GTGTATTT | GTGTATTT | 1 |
| TGGTAGTT | TGGTAGTG | 1 | TGTTAAGC | TTATAGGC | 1 |
| GGTTACAT | GGCTATGT | 1 | GAGTAGTC | GAGTAGTG | 1 |
| GTCTAGCG | GCCTAGCG | 1 | CGGTATGC | GGGTATGA | 1 |
| GTGTAGCT | GAGTACGT | 1 | GCTTAAGA | GGGTAAGA | 1 |
| GGGTACGG | GGGTATGG | 1 | CGGTAGGT | GGGTAGGC | 1 |
| GCGTATGG | GCGTACGG | 1 | GGGTAGTT | GGGTAGGT | 1 |
| AAATAGCC | AGTTAGCC | 1 | GTGTAATG | GCGTAGGG | 1 |
| TCGTAGCG | GCGTAGCT | 1 | GGGTAGAC | GGGTAGAC | 1 |
| TAGTAGGT | GAGTAGGT | 1 | GGGTATTT | GGGTATTG | 1 |
| GGGTAAGC | GGGTACTC | 1 | TTGTACGC | ATGTACGG | 1 |
| GTGTAAAT | GCCTAAAT | 1 | GGGTACGA | GTGTATGA | 1 |
| GGGTATCG | GGGTATGG | 1 | GGGTAGTG | GGGTAGTG | 1 |
| GGTTAAGC | GGGTAGGC | 1 | TCTTATGC | TTTTATGC | 1 |
| TGGTAGTC | GGGTAGTA | 1 | GTGTAGTG | GAGTATGG | 1 |
| GTGTACGG | GTTTACGG | 1 | GAGTAGTG | TAGTAGTA | 1 |
| GTGTAGCT | GGGTATTT | 1 | GTTTACGC | GTTTACGA | 1 |
| GGGTAGTT | GGGTAGTT | 1 | TGGTATGT | GGGTATGG | 1 |
| TGGTAGGA | TGGTAGGG | 1 | TTGTAGGA | CTGTAGGC | 1 |
| TGGTAATT | GGGTAATG | 1 | TGGTAGGA | AGGTAGGC | 1 |
| GGGTAGTG | GGGTAGAG | 1 | GCCTACGC | GGATAGGC | 1 |
| TTGTAGTC | GTGTAGTG | 1 | TTGTACGC | GTGTACGC | 1 |
| TGGTATGT | GGGTATGC | 1 | TGGTAGGG | GGGTAGGA | 1 |
| GGGTATTC | GGGTATTC | 1 | GCTTAGCG | TCTTAGCA | 1 |

TABLE IV

Unique Non-Self Mutant LoxP Spacer Pairs

| LE | RE | No. Occurrences | LE | RE | No. Occurrences |
|---|---|---|---|---|---|
| TGGTAGGC | TGGTAGGT | 4 | TGGTACGC | TGTTATAC | 1 |
| GGGTATGC | GGGTATGG | 3 | GGGTATCG | GTGTAAGG | 1 |
| GTGTAGTT | GTGTAGTG | 3 | TGGTAGTA | GGGTAGTA | 1 |
| GGGTATGG | GTGTATGG | 2 | GTGTAGAC | GTGTAGAA | 1 |

TABLE IV-continued

Unique Non-Self Mutant LoxP Spacer Pairs

| LE | RE | No. Occurrences | LE | RE | No. Occurrences |
|---|---|---|---|---|---|
| TGGTAGTC | TGGTAGTG | 2 | GAGTAGGG | AAGTAGGC | 1 |
| GTGTACGG | GTGTACGC | 2 | GAGTAAAT | GGTTACGT | 1 |
| TGGTAGGA | GGGTAGGA | 2 | GGCTACGC | GGGTACGC | 1 |
| GGGTATAC | GTGTATAC | 2 | TGTTACGT | CGTTACGC | 1 |
| GGGTAAGT | GGGTATGT | 2 | GCATAGAT | GCATAGAC | 1 |
| TGGTAGTC | GGGTAGTC | 2 | TGTTAGTG | TTGTAGGG | 1 |
| GTGTAAGA | GTGTAAGG | 2 | GGGTAAGA | GGGTAAGG | 1 |
| GGGTATGA | GGGTAGGA | 2 | GCGTAGGT | GTGTAGGT | 1 |
| GGGTATAC | GGCTAGGC | 2 | GGGTATTA | GGGTATGA | 1 |
| GAGTAGGA | GAGTAGGG | 2 | GGGTATGA | GGGTATGG | 1 |
| TTGTAGGC | CTGTAGGG | 2 | GAGTAGGT | GCGTAGGT | 1 |
| TGGTAGTC | CGGTAGTT | 1 | TGATATGG | AGATATGT | 1 |
| TTGTATGT | GTGTATGT | 1 | GGGTAGAA | TGGTAGAG | 1 |
| TTGTATTC | GTGTATTA | 1 | TCGTAGTG | GCGTAGTC | 1 |
| GCGTATGC | GATTAGGC | 1 | GTACGCG | GGATATGC | 1 |
| GCGTAGGT | GGGTAAAT | 1 | TTGTAAGT | CTGTAAGC | 1 |
| GCGTATAT | GCTTATGT | 1 | TCATAGTC | GCATAGTA | 1 |
| TGGTATCA | GGGTATCC | 1 | GGGTATGT | GATTAGGT | 1 |
| TGTTAGGC | AGTTAGGT | 1 | GCGTAGGT | ACGTAGGG | 1 |
| TGGTAGGT | CGGTAGGA | 1 | GCATAGTA | GCATACTA | 1 |
| GGATAGGC | GGGTACGC | 1 | GGATAAGT | GGCTAGAT | 1 |
| GTGTATCG | GTGTAATG | 1 | GGGTAGGA | GTTTAGGA | 1 |
| TGGTAAGC | GGGTAAGA | 1 | TACTAGAC | GACTAGAC | 1 |
| TGGTACGT | GGGTACGT | 1 | GGTTAAGT | GGATAACT | 1 |
| GGATAGCC | GTGTAGAC | 1 | TGGTAGGC | TGGTAGCC | 1 |
| TGGTAGTA | TGGTAGAA | 1 | TTGTAGCA | TGGTAGCA | 1 |
| ATGTAGGG | CTGTAGGC | 1 | GAGTAGGT | AAGTAGGC | 1 |
| GTGTAGTT | GCGTAGGT | 1 | GCATATGC | GGGTATGC | 1 |
| GAGTATGA | GGGTATTA | 1 | TGTTATGC | GGTTATGG | 1 |
| GCGTAATG | GCGTACAG | 1 | TCATAGAA | TGATACGA | 1 |
| GTGTACGT | GTGTAGGT | 1 | TGGTACGC | TGGTACGG | 1 |
| TCGTAGGT | CCGTAGGT | 1 | GTTTACAT | GTTTAGAT | 1 |
| GTGTAATG | GTATAGTG | 1 | GGGTAGCC | GGGTACGC | 1 |
| TCGTAGGA | GCGTAGGA | 1 | GTGTATGA | CTGTATGG | 1 |
| GCGTAGAC | GTGTAGAC | 1 | GGCTAGGA | GGGTAGGA | 1 |
| TGGTAGCG | TACTATGG | 1 | GAGTATAC | GAGTATAG | 1 |
| GGGTAACT | GTGTATGT | 1 | GGATAAGT | GGCTAGGT | 1 |
| TGCTAGTG | GGCTAGTG | 1 | TACTACTC | GACTACTA | 1 |
| TCGTATTG | TCGTAGGG | 1 | AGCTAGGG | GGCTAGGA | 1 |
| GGGTATGT | GACTAAAT | 1 | GCGTAATG | GCGTAGTG | 1 |
| GCGTAGGC | GGATAGGC | 1 | CGGTATGC | GGGTATGG | 1 |
| GTGTAGCC | CTGTAGCC | 1 | GACTAGCG | GTGTATGG | 1 |
| TGGTAGGA | AGGTAGGG | 1 | GCGTAAGG | GCGTAGGG | 1 |
| GTGTACAT | GGTTATAT | 1 | GCGTACGC | ACGTACGT | 1 |
| TGGTACGT | GGGTACGC | 1 | GGCTATTC | GGGTACGC | 1 |
| GCTTAGTC | GGGTACGC | 1 | GCATACGA | GGATAGGA | 1 |
| GAGTATGC | GGGTATGC | 1 | GGGTAGGA | GGGTAACA | 1 |
| TGGTAATC | GGGTAATG | 1 | GGCTAGGA | AGCTAGGC | 1 |
| TGCTAGTT | GGCTAGTT | 1 | TCGTAGGA | GCGTAGGT | 1 |
| GCATATGC | GGCTACGC | 1 | GGGTAAGT | GGATAATT | 1 |
| GGATAGGC | AGATAGGG | 1 | GGGTACTA | GGGTACTG | 1 |
| GGATACGC | GTGTAAGC | 1 | TTTTATGG | TTATATTG | 1 |
| AGTTAGGG | AGGTAAGG | 1 | TGGTAGGT | GGGTAGGA | 1 |
| GAGTAGCG | CAGTAGCC | 1 | GAGTAGGC | GAGTAGGG | 1 |
| GGGTATGT | GGTTAGCT | 1 | TTGTACGC | GTGTACGA | 1 |
| GGCTATGG | AGCTATGC | 1 | TGATAGGT | TCGTAGGT | 1 |
| GAATAGCC | GAATAGCG | 1 | GATTAGGC | GAGTATGC | 1 |
| GGCTAACG | GGGTATTG | 1 | TGGTAGCG | TTATAGGG | 1 |
| GGCTAGGT | GGATAGCT | 1 | GCGTAGTT | GCGTAAGT | 1 |
| TGGTACGT | AGGTACGG | 1 | GTTTAGCC | GAGTAGTC | 1 |
| GGGTAATT | GGGTAATC | 1 | GGGTAGCC | GTTTATGC | 1 |
| TGGTATGG | GGGTATGG | 1 | GCGTAGAC | GTGTACTC | 1 |
| GACTAAGC | GAGTAAGC | 1 | TAGTAGGC | TAGTAGGG | 1 |
| GCGTAGGC | GCGTAGGG | 1 | GAGTAGGA | CAGTAGGC | 1 |
| TGATACGC | CGATACGG | 1 | GGGTACCC | GCTTAGCC | 1 |
| TGGTAGGC | TGGTAAAC | 1 | TGGTAGAT | GGGTAGAG | 1 |
| AGATATGG | GGATATGC | 1 | TTTTATGG | GTTTATGA | 1 |
| TTGTAGTC | CTGTAGTC | 1 | GAGTAGGC | GGGTATGC | 1 |
| TTCTATGC | GTCTATGT | 1 | GCGTATGC | GCGTATGG | 1 |
| TGGTACGC | GGGTACGT | 1 | GTTTAGTT | GTTTAGTG | 1 |
| GTCTAGCG | GTGTAGCG | 1 | TTGTAGGC | ATGTAGGG | 1 |
| GTGTAAGC | GTGTAAGG | 1 | TGGTAGGC | AGGTAGGG | 1 |
| GTGTAATG | GTGTAGCG | 1 | GTCTAAAT | GCTTAGGT | 1 |

TABLE IV-continued

Unique Non-Self Mutant LoxP Spacer Pairs

| LE | RE | No. Occurrences | LE | RE | No. Occurrences |
|---|---|---|---|---|---|
| GGATATAT | GGGTATGT | 1 | GCGTATGA | GAATATGA | 1 |
| GTGTATTG | GTTTAAAG | 1 | GGCTAGGG | CGCTAGGC | 1 |
| TTGTAGAC | GTGTAGAA | 1 | GGGTAGCA | GGGTAGGA | 1 |
| GGATAGAC | GTGTAGAC | 1 | GACTAGCC | GATTAGGC | 1 |
| GGGTACGA | GGGTACGC | 1 | GCTTAGCC | GGTTAGTC | 1 |
| ATTTACGA | AGTTATGA | 1 | GGCTATGG | GGCTATGT | 1 |
| GGATATTG | GGGTATGG | 1 | TGTTAGAT | AGTTAGAG | 1 |
| TTTTAAGA | TTGTAGGA | 1 | TCTTATGC | GCTTATGG | 1 |
| GGGTATAT | GGGTAACT | 1 | TGGTACGA | TGGTACGC | 1 |
| GGGTATAC | GGGTATGC | 1 | TGCTAGGA | CGCTAGGT | 1 |
| GTGTAGCG | GTTTAGGG | 1 | GGGTACGT | TGGTACGG | 1 |
| GCTTAGGG | GCATAACG | 1 | GGGTAGTC | GGGTACCC | 1 |
| GTTTAGGC | GCGTAGGC | 1 | GTTTAAGC | GTTTATGC | 1 |
| TGGTACGC | AGGTACGC | 1 | TTGTAGCC | GTGTAGCT | 1 |
| GCATAGAG | GTGTAGTG | 1 | GCGTATGA | GCGTAGGA | 1 |
| TGGTAGGC | CGGTAGGC | 1 | GGCTATGC | GGGTATGC | 1 |
| CAGTAACC | CTGCATCC | 1 | GCATAGGT | GCGTATTT | 1 |
| GGATAGGG | GTCTATAG | 1 | GCGTAGGA | GCGTAGCA | 1 |
| AAGTACTT | AAGTAATT | 1 | GTGTAAGG | GAGTAGAG | 1 |
| TGGTAGAT | TTGTAGTT | 1 | TTGTAAGC | GTGTAAGA | 1 |
| GGGTACGT | GGGTACGG | 1 | GCTTAGAT | GCTTAGAG | 1 |
| GTGTACTC | GGATAGGC | 1 | AGATATGC | GGATATGA | 1 |
| GCGTATAT | GTGTATAT | 1 | GGCTAGAC | GGCTAGTC | 1 |
| GGCTAGTT | GGGTACAT | 1 | TGGTAGTC | TTGTAGGC | 1 |
| TTGTAGGA | GTGTAGGT | 1 | GTCTAGGG | GTGTAAGG | 1 |
| GGTTAATG | GGGTAATG | 1 | GAGTATGA | TAGTATGA | 1 |
| GCGTAGCG | GGTTAGTG | 1 | GCGTAGGG | GGGTAACG | 1 |
| TGGTACAC | GGGTACAT | 1 | TGTTATGG | TCGTAGGG | 1 |
| CACTATGC | AACTATGG | 1 | TGTTAGGC | GGTTAGGG | 1 |
| TCGTAGGG | CCGTAGGT | 1 | TGGTAGGC | TTGTATAC | 1 |
| GGGTATTG | GGTTAGAG | 1 | GAGTAGGA | CAGTAGGA | 1 |
| GCGTAGGG | CCGTAGGG | 1 | GCGTACAT | GGGTATGT | 1 |
| GGATAGGG | GTTTAGGG | 1 | GGTTATTT | GGTTAGTT | 1 |
| GCGTAGGA | GAGTAGGA | 1 | GTGTAAGT | GTGTAGGT | 1 |
| GGGTATGC | TGGTATGG | 1 | TGCTAGGG | TGTTAGTG | 1 |
| GCTTACGA | GGGTAGGA | 1 | GGATAGGT | GGATAGGA | 1 |
| GTGTATTG | GTTTAGGG | 1 | GGGTAATA | GGGTATGA | 1 |
| GCTTAGTA | GCGTAGGA | 1 | TGATAGGC | TTGTAGGC | 1 |
| TAGTAGGA | AAGTAGGG | 1 | GGGTACGT | GTATAGGT | 1 |
| TGGTAGAG | TAGTACGG | 1 | GAGTACGG | CAGTACGT | 1 |
| TGGTACGC | TGGTAGGC | 1 | TTGTAGTA | GTGTAGTA | 1 |
| GGATAGGC | GGATAGGG | 1 | TGGTAGGT | CGGTAGGC | 1 |
| GGGTATGT | GCGTATCT | 1 | GGCTATAC | GGGTATGC | 1 |
| TAGTATGT | GAGTATGG | 1 | GCGTAGGA | TCGTAGGG | 1 |
| TGGTATGA | GGGTATGG | 1 | GATTAGGA | GGGTAGGA | 1 |
| GGCTAAAG | GAATATGG | 1 | TTATACGA | TGTTAGGA | 1 |
| GTGTAAGC | GTGTAAGT | 1 | AGGTAGAC | GGGTAGAG | 1 |
| CAGTATGC | GAGTATGA | 1 | GCGTAGTG | GCCTAGGG | 1 |
| GTATAGGA | GACTAGGA | 1 | CCCTAGGA | CGTTAGCA | 1 |
| GGGTAACG | GGGTACTG | 1 | ACGTAGGC | GCGTAGGC | 1 |
| TGCTAGTG | GGCTAGTT | 1 | TTTTACAC | TTGTAGGC | 1 |
| AGGTACAC | GGGTACAG | 1 | TGCTACAG | TGATAAAG | 1 |
| GATTAGGC | CATTAGGT | 1 | GCGTAGTC | GACTATGC | 1 |
| GCGTAGGT | GTGTAAGT | 1 | TATTACTG | TCGTAGCG | 1 |
| GGGTACGC | GGGTAGTC | 1 | TTATAGCG | GTATAGCC | 1 |
| CGGTATGT | TGGTATGG | 1 | GCGTATGC | GAGTATGC | 1 |
| TGGTAGTG | GGGTAGTA | 1 | GGGTACGC | GGGTACGG | 1 |
| GTTTAGGG | TTTTAGGA | 1 | GTGTATGG | GCATAGCG | 1 |
| TTGTAGGC | TAGTAGGC | 1 | TGGTACGA | AGGTACGT | 1 |
| TGGTAGAG | TTGTAAGG | 1 | GGGTACAG | GAGTATGG | 1 |
| GGTTACAT | GGCTATGT | 1 | TGTTAGCA | AGTTAGCG | 1 |
| GTCTAGCG | GCCTAGCG | 1 | GGGTATAT | GGGTAAGT | 1 |
| GTGTAGCT | GAGTACGT | 1 | TGGTAATC | TGGTAATG | 1 |
| GGGTACGG | GGGTATGG | 1 | AAGTAGGG | GAGTAGGG | 1 |
| GCGTATGG | GCGTACGG | 1 | GAGTAGGC | GCTTATGC | 1 |
| AAATAGCC | AGTTAGCC | 1 | GCGTAAAA | GCGTAGGA | 1 |
| TCGTAGCG | GCGTAGCT | 1 | TCGTAGAG | GCGTAGAG | 1 |
| TAGTAGGT | GAGTAGGT | 1 | GGGTACGG | TGGTACGG | 1 |
| GTGTAAAT | GCCTAAAT | 1 | GGCTAATG | GGCTAGGG | 1 |
| GGGTATCG | GGGTATGG | 1 | GAGTAGGC | GTTTATGC | 1 |
| TGGTAGTC | GGGTAGTA | 1 | TGATAGTC | CGATAGTC | 1 |
| GTGTACGG | GTTTACGG | 1 | GGTTAGTT | GGGTAAAT | 1 |
| GTGTAGCT | GGGTATTT | 1 | GGCTAGGC | GTATAGGC | 1 |

TABLE IV-continued

Unique Non-Self Mutant LoxP Spacer Pairs

| LE | RE | No. Occur-rences | LE | RE | No. Occur-rences |
|---|---|---|---|---|---|
| TGGTAATT | GGGTAATG | 1 | TGTTAAGC | TTATAGGC | 1 |
| TTGTAGTC | GTGTAGTG | 1 | GAGTAGTC | GAGTAGTG | 1 |
| GCGTAAGT | ACGTAAGG | 1 | CGGTATGC | GGGTATGA | 1 |
| GCTTAGGG | GGATATGG | 1 | GCTTAAGA | GGGTAAGA | 1 |
| GATTACGG | TATTACGC | 1 | GTGTAATG | GCGTAGGG | 1 |
| TCGTATGT | CCGTATGT | 1 | GGGTATTT | GGGTATTG | 1 |
| GGTTACGC | GTTTACGC | 1 | TTGTACGC | ATGTACGG | 1 |
| GGCTAGGT | TGCTAGGG | 1 | GGGTACGA | GTGTATGA | 1 |
| GGATAGCA | TGATAGCC | 1 | TCTTATGC | TTTTATGC | 1 |
| TGGTAACG | TTGTAGTG | 1 | GTGTAGTG | GAGTATGG | 1 |
| GAGTAGGT | AAGTAGGT | 1 | GAGTAGTG | TAGTAGTA | 1 |
| TTGTAGAC | GTGTAGAC | 1 | GTTTACGC | GTTTACGA | 1 |
| GCATAAGC | GAATAGGC | 1 | TTGTAGGA | CTGTAGGC | 1 |
| GGTTAGGT | GATTAGGT | 1 | TGGTAGGA | AGGTAGGC | 1 |
| TAGTATGC | TGGTAAGC | 1 | GCCTACGC | GGATAGGC | 1 |
| TGCTAGGC | GGCTAGGG | 1 | TTGTACGC | GTGTACGC | 1 |
|  |  |  | GCTTAGCG | TCTTAGCA | 1 |

What is claimed is:

1. A kit for carrying out multiple non-cross reacting recombination reactions, the kit comprising at least one pair of mutant loxP recombination elements selected from the group of pairs defined by the formula: a first member of a pair is defined in a 5'→3' orientation as:

$LE_1$-$S_1$-$RE_1$ and a second member of the pair is defined in a 5'→3' orientation as:

$LE_2$-$S_2$-$RE_2$ where:

$LE_1$ is a mutant or wild type left inverted repeat of a loxP recombination element and $RE_1$ is a mutant or wild type right inverted repeat of a loxP recombination element such that whenever $LE_1$ is a wild type sequence, $RE_1$ is a mutant sequence, and whenever $LE_1$ is a mutant sequence, $RE_1$ is a wild type sequence;

$LE_2$ is a mutant or wild type left inverted repeat of a loxP recombination element and $RE_2$ is a mutant or wild type right inverted repeat of a loxP recombination element such that whenever $LE_2$ is a wild type sequence, $RE_2$ is a mutant sequence, and whenever $LE_2$ is a mutant sequence, $RE_2$ is a wild type sequence; with the proviso that whenever $LE_1$ is a mutant sequence, then $LE_2$ is a wild type sequence and whenever $LE_1$ is a wild type sequence, then $LE_2$ is a mutant sequence; and $S_1$ and $S_2$ are each a mutant loxP spacer region each having the same sequence in a 5'→3' orientation selected from the group consisting of: GTATAGTA, GGCTATAG, TCGTAGGC, GTGTATTT, GTGTACGG, GCGTATGT, TTGTATGG, GGATAGTA, AGGTATGC, GGTTACGG, TTTTAGGT, GAGTACGC, and GTGTACGC, or, $S_1$ is GTGTACGC whenever $S_2$ is GTGTACGG, and $S_2$ is GTGTACGC whenever $S_1$ is GTGTACGG.

2. The kit of claim 1 wherein $LE_1$ is lox71 left inverted repeat region and $RE_1$ is a wild type right inverted repeat of a loxP recombination element and wherein $RE_2$ is lox66 right inverted repeat region and $LE_2$ is a wild type left inverted repeat region of a loxP recombination element.

3. The kit of claim 2 wherein said first and second members of each of said pairs, are in different vectors.

4. The kit of claim 1 further including a Cre recombinase and a Cre recombinase buffer.

5. The kit of claim 1 wherein said first and second members of each of said pairs are in different vectors.

6. The kit of claim 1 further including a plasmid carrying a gene encoding a Cre recombinase and a regulatory element permitting inducible expression of the gene encoding the Cre recombinase.

7. The kit of claim 6 wherein at least one of said vectors carrying each of said pairs of said first and second members has a selectable marker.

8. A kit for carrying out multiple non-cross reacting recombination reactions, the kit comprising at least one pair of mutant loxP recombination elements selected from the group of pairs defined by the formula: a first member of a pair is defined in a 5'→3' orientation as:

$LE_1$-$S_1$-$RE_1$ and a second member of the pair is defined in a 5'→3' orientation as:

$LE_2$-$S_2$-$RE_2$ where:
  $LE_1$ is a mutant or wild type left inverted repeat of it loxP recombination element and $RE_1$ is a mutant or wild type right inverted repeat of a loxP recombination element such that whenever $LE_1$ is a wild type sequence, $RE_2$ is a mutant sequence, and whenever $LE_1$ is a mutant sequence, $RE_1$ is a wild type sequence;
  $LE_2$ is a mutant or wild type left inverted repeat of a loxP recombination element and $RE_2$ is a mutant or wild type right inverted repeat of a loxP recombination element such that whenever $LE_2$ is a wild type sequence, $RE_2$ is a mutant sequence, and whenever $LE_2$ is a mutant sequence, $RE_2$ is a wild type sequence;
  wherein each such pair of loxP recombination elements react with one another to produce a recombinant that has a loxP site having a mutant left inverted repeat and a mutant right inverted repeat and a loxP site having a mutant-free left inverted repeat and a mutant-free right inverted repeat; and
  $S_1$ and $S_2$ are each a mutant loxP spacer region each having the same sequence in a 5'→3' orientation selected from the group consisting of: GTATAGTA, GGCTATAG, TCGTAGGC, GTGTATTT, GTGTACGG, GCGTATGT, TTGTATCG, GGATAGTA, AGGTATGC, GGTTACGG, TTTTAGGT, GAGTACGC, and GTGTACGC, or, $S_1$ is GTGTACGC whenever $S_2$ is GTGTACGG; and $S_2$ is GTGTACGC whenever $S_1$ is GTGTACGG.

9. The kit of claim 8 wherein $LE_1$ is lox71 left inverted repeat region and $RE_1$ is a wild type right inverted repeat of a loxP recombination element and wherein $RE_2$ is lox66 right inverted repeat region and $LE_2$ is a wild type left inverted repeat region of a loxP recombination element.

10. The kit of claim 9 wherein said first and second members of each of said pairs are in different vectors.

11. The kit of claim 9 further including a Cre recombinase and a Cre recombinase buffer.

12. The kit of claim 11 wherein said first and second members of each of said pairs are in different vectors.

13. The kit of claim 12 further including a plasmid carrying a gene encoding a Cre recombinase and a regulatory element permitting inducible expression of the gene encoding the Cre recombinase.

14. The kit of claim 13 wherein at least one of said vectors carrying each of said pairs of said first and second members has a selectable marker.

* * * * *

SEQUENCE LISTING

```
<160> NUMBER OF SEQ ID NOS: 10

<210> SEQ ID NO 1
<211> LENGTH: 34
<212> TYPE: DNA
<213> ORGANISM: Escherichia coli

<400> SEQUENCE: 1
ataacttcgt ataatgtatg ctatacgaag ttat                              34

<210> SEQ ID NO 2
<211> LENGTH: 34
<212> TYPE: DNA
<213> ORGANISM: Escherichia coli

<400> SEQUENCE: 2
ataacttcgt ataatgtata ctatacgaag ttat                              34

<210> SEQ ID NO 3
<211> LENGTH: 34
<212> TYPE: DNA
<213> ORGANISM: Escherichia coli

<400> SEQUENCE: 3
ataacttcgt ataatgtgta ctatacgaag ttat                              34

<210> SEQ ID NO 4
<211> LENGTH: 34
<212> TYPE: DNA
<213> ORGANISM: Escherichia coli

<400> SEQUENCE: 4
ataacttcgt ataaagtatc ctatacgaag ttat                              34

<210> SEQ ID NO 5
<211> LENGTH: 34
<212> TYPE: DNA
<213> ORGANISM: Escherichia coli
```

-continued

```
<400> SEQUENCE: 5
ataacttcgt ataagaaacc atatacgaag ttat                            34

<210> SEQ ID NO 6
<211> LENGTH: 34
<212> TYPE: DNA
<213> ORGANISM: Escherichia coli

<400> SEQUENCE: 6
ataacttcgt atataatacc atatacgaag ttat                            34

<210> SEQ ID NO 7
<211> LENGTH: 34
<212> TYPE: DNA
<213> ORGANISM: Escherichia coli

<400> SEQUENCE: 7
ataacttcgt ataagataga atatacgaag ttat                            34

<210> SEQ ID NO 8
<211> LENGTH: 34
<212> TYPE: DNA
<213> ORGANISM: Escherichia coli

<400> SEQUENCE: 8
ataacttcgt atacgatacc atatacgaag ttat                            34

<210> SEQ ID NO 9
<211> LENGTH: 34
<212> TYPE: DNA
<213> ORGANISM: Escherichia coli

<400> SEQUENCE: 9
taccgttcgt ataatgtatg ctatacgaag ttat                            34

<210> SEQ ID NO 10
<211> LENGTH: 34
<212> TYPE: DNA
<213> ORGANISM: Escherichia coli

<400> SEQUENCE: 10
ataacttcgt ataatgtatg ctatacgaac ggta                            34
```